US006512006B1

(12) United States Patent
Boyer, Jr. et al.

(10) Patent No.: US 6,512,006 B1
(45) Date of Patent: Jan. 28, 2003

(54) HIV PROTEASE INHIBITORS

(75) Inventors: Frederick Earl Boyer, Jr., Canton Township, MI (US); John Michael Domagala, Canton, MI (US); Edmund Lee Ellsworth, Brighton, MI (US); Christopher Andrew Gajda, Ann Arbor, MI (US); Elizabeth Ann Lunney, Ann Arbor, MI (US); Alexander Pavlovsky, Ann Arbor, MI (US); Vara Prasad Venkata Nagendra Josyula, Ann Arbor, MI (US); Bradley Dean Tait, Killingworth, CT (US)

(73) Assignee: Warner-Lambert Company, Ann Arbor, MI (US)

( * ) Notice: Subject to any disclaimer, the term of this patent is extended or adjusted under 35 U.S.C. 154(b) by 0 days.

(21) Appl. No.: 09/641,260

(22) Filed: Aug. 17, 2000

Related U.S. Application Data

(60) Provisional application No. 60/169,754, filed on Dec. 9, 1999.

(51) Int. Cl.$^7$ .................... C07D 309/30; A61K 31/352; A61P 31/18; A61P 31/12
(52) U.S. Cl. .................... 514/460; 546/192; 549/292
(58) Field of Search .................... 549/292; 514/460; 546/192, 282.1, 139, 152; 548/146, 206, 215, 240, 266.6, 250, 255, 364.1, 518, 207, 217, 361.1; 544/149, 238, 333, 405, 359, 59, 283, 353

(56) References Cited

U.S. PATENT DOCUMENTS 5,789,440 A * 8/1998 Ellsworth et al. ........... 514/460
5,834,506 A * 11/1998 Boyer, Jr. et al. .......... 514/460

FOREIGN PATENT DOCUMENTS

WO         WO0015625        * 3/2000

OTHER PUBLICATIONS

Navia and McKeever, "A Role for the Aspartyl Protease from the Human Immunodeficiency Virus Type 1 (HIV–1) in the Orchestration of Virus Assembly", *New York Acad. Sci.*, 1990; 616:73–85.*
von der Helm, "Retroviral Proteases: Structure, Function and Inhibition From a Non–Anticipated Viral Enzyme to the Target of a Most Promising HIV Therapy", *Biol. Chem.*, 1996; 377–765–774.*

Deeks et al., "HIV–1 Protease Inhibitors", *JAMA*, 1997; 277:145–153.*
Barry et al., "Protease Inhibitors in Patients with HIV Disease", *Clin. Pharmacokinet.*, 1997; 32:194–209.*
Schock et al., "Mutational Anatomy of an HIV–1 Protease Variant Conferring Cross–resistance to Protease Inhibitors in Clinical Trials", *J. Biol. Chem.*, 1996; 271:31957–31963.*
Fätkenheuer et al., "Virological treatment failure of protease inhibitor therapy in an unselected cohort of HIV–infected patients", *AIDS*, 1997; 11:F113–F116.*
Wallace, "New HIV protease inhibitors", *DDT*, 1997; 2:83–84.*
Tummino et al., "Discovery and Optimization of Nonpeptide HIV–1 Protease Inhibitors", *Bioorganic & Med. Chem.*, 1996; 4:1401–1410.*
Tait et al., "4–Hydroxy–5,6–dihydropyrones. 2. Potent Non–Peptide Inhibitors of HIV Protease", *J. Med. Chem.*, 1997; 40:3781–3792.*
Hagen et al., "Synthesis of 5,6–Dihydro–4–hydroxy–2–pyrones as HIV–1 Protease Inhibitors: The Profound Effect of Polarity on Antiviral Activity", *J. Med. Chem.*, 1997; 40:3707–3711.*
Vander Roest et al., "Pharmacokinetic evaluation for a series of dihydropyrone HIV protease inhibitors in mice", 37$^{th}$ *Interscience Conference on Antimicrobial Agents and Chemotherapy*, Sep. 8—Oct. 1, 1997, Toronto, Canada. Abstract I–84.*
Domagala et al., "PD 178390: A Novel Potent Non Peptide HIV Protease Inhibitor of the 5,6–Dihydro–4–hydroxy–2–pyrone Class", 5$^{th}$ *Conference on Retroviruses and Opportunistic Infections*, Feb. 1–5, 1998, Chicago, Illinois. Abstract 638.*
Thaisrivongs et al., "Structure–Based Design of HIV Protease Inhibitors: Sulfonamide–Containing 5,6–Dihydro–4–hydroxy–2–pyrones as Non–Peptide Inhibitors", *J. Med. Chem.*, 1996; 39:4349–4353.*
Copending USSN 09/674,381 filed Oct. 31, 2000.*

* cited by examiner

Primary Examiner—Richard L. Raymond
Assistant Examiner—Kahsay Habte
(74) Attorney, Agent, or Firm—Elizabeth M. Anderson; Heidi M. Berven

(57) ABSTRACT

The present invention related to novel dihydropyrones possessing 3-position nitrogen atom, which inhabit the HIV aspartyl protease blocking HIV infectivity. The dihydropyrones are useful in the development of therapies for the treatment of viral infections, and diseases, including AIDS.

20 Claims, No Drawings

HIV PROTEASE INHIBITORS

This application claims the benefit of Provisional Application No. 60/169,754 filed Dec. 9, 1999.

BACKGROUND OF THE INVENTION

The HIV-protease enzyme is absolutely essential for the replication and dissemination of HIV throughout the body (Navia M. A. and McKeever B. M., *Ann. New York Acad. Sci.,* 1990; 616:73–85) and has become an extremely important target for the design and development of anti-HIV therapeutic agents (von der Helm K., *Biol. Chem.* 1996; 377:756–774). Several peptidomimetic HIV protease inhibitors have been successfully developed (such as indinavir, saquinavir, ritonavir, and nelfinavir), which demonstrate significant clinical success in lowering plasma viral load, reducing the onset to AIDS, and decreasing the frequency of opportunistic infections (Deeks S. G., Smith M., Holodniy M., and Kahn J. O., *JAMA.* 1997; 277:145–153).

Yet the current HIV protease inhibitors by their peptidomimetic nature have relatively poor solubility, high biliary excretion, limited bioavailabilities and significant liver metabolism. These drawbacks in turn increase the need for high doses of a drug, which increases the frequency of various side effects and multiple drug interactions (Barry M., Gibbons S., Back D., and Mulcahy F., *Clin. Pharmacokinet.,* 1997;32: 194–209). More importantly, resistance to the current HIV protease inhibitors has emerged (Shock H. B., Garsky V. M., and Kuo L., *J. Biol. Chem.,* 1996;271:31957–31963) resulting in treatment failures (Fatkenheuer G., Theisen A., Rockstroh J., Grabow T., et al., AIDS, 1997;11:F113–F116). From this discussion, it is apparent that while HIV protease is an excellent antiviral target for the treatment of HIV infection and AIDS, there is a need to identify non-peptide inhibitors with improved pharmacological properties and which are not cross resistant with the current drugs (Wallace R. W., *DDT,* 1997;2:83–84).

U.S. Pat. No. 5,789,440 recites non-peptidic HIV protease inhibitors of formula A

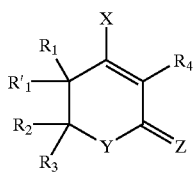

A

The patent is hereby incorporated by reference. Excellent HIV protease inhibition was achieved, but the antiviral activity at the cellular level was in some cases less than desired for an ideal therapeutic agent due to poor overall pharmacological properties (Tummino P. J., Vara Prasad J. V. N., Ferguson D., Nauhan C., et al., *BioOrganic and Med Chem.,* 1996;4:1401–1410). These efforts however led to a core structure B where $R_1$ and $R_2$ were alkyl groups filling the

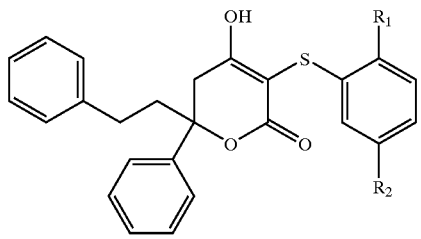

B $S_1'$ and $S_2'$ pockets, respectively, and the phenyl of the phenethyl group at $C_6$ filled the $S_2$ pocket very efficiently. This core structure was recognized as a valuable platform for additional study (Tait B. D., Hagen S., Domagala J. M., Ellsworth E. L., et al., *J. Med. Chem.,* 1997;40:3781–3792).

Additional dihydropyrones C were reported when it was unexpectedly discovered that certain groups which reduced lipophilicity judiciously placed at $R_1$–$R_5$ led to greatly

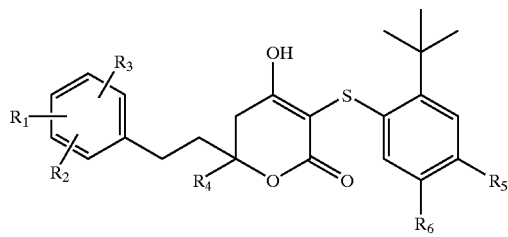

C improved antiviral cellular activity. See U.S. Pat. No. 5,834, 506. The patent is hereby incorporated by reference. Among the preferred compounds were those where $R_1$ and $R_5$ were OH, $NH_2$, or $CH_2OH$. In such cases, the preferred $R_4$ included a small alkyl chain or ring and $R_6$ was methyl. In addition to improved cellular antiviral activity, the compounds also showed good pharmacokinetics in animals relative to the less-polar substituted compounds. These compounds were also not cross resistant with current HIV Protease inhibitors (Hagen S. E., Vara Prasad J. V. N., Boyer F. E., Domagala J. M ., et al., *J. Med.,* 1997;40:3707–3711; Vander Roest S., Wold S., and Saunders J., 37th *Interscience Conference on Antimicrobial Agents and Chemotherapy,* Sep. 28–Oct. 1, 1997, Toronto, Canada. Abstract I-84; Domagala J. M., Boyer F., Ellsworth E., Gajda C., et al., 5th *Conference on Retroviruses and Opportunistic Infections,* Feb. 1–5, 1998, Chicago, Ill. Abstract 638).

While the compounds C were notable for their improved pharmacological properties relative to the non-polar substituted core molecules B, these highly favorable properties were conferred directly by the use of OH, $NH_2$ and $NR_2$ groups placed on the lipophilic rings. The rings themselves were important for binding to the enzyme "pockets" and for holding the t-butyl group and the groups $R_1$–$R_3$ and $R_5$ in their proper places within the enzyme's active site.

This hereby incorporates by reference 5888L1-01-TMC filed on even date herewith entitled "A Method of Making Dihydropyrone HIV Protease Inhibitors" by Victor Fedij et al.

SUMMARY OF THE INVENTION

The present invention relates to compounds or pharmaceutically acceptable salts thereof of formula I, shown below:

FORMULA I

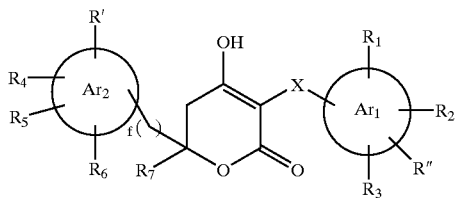

wherein:
R₁ is H, a straight or branched alkyl of 1–6 carbons or a carbocycle of 3–6 carbons,
R₂ is H, a straight or branched alkyl of 1–5 carbons or a carbocycle of 3–6 carbons;
R₃ is H [C(R₉)₂]ₙOR, [C(R₉)₂]ₙN(R)₂, [C(R₉)₂]ₙN(R₉)COR, [C(R₉)₂]ₙCO₂R, [C(R₉)₂]ₙ(O)COR, [C(R₉)₂]ₙCON(R)₂, [C(R₉)₂]ₙOC(O)N(R)₂, [C(R₉)₂R], [C(R₉)₂]ₙN(R₉)CON(R)₂, [C(R₉)₂]ₙN(R₉)CO₂R, [C(R₉)₂]ₙOSO₂N(R)₂, [C(R₉)₂]ₙN(R₉)SO₂OR, [C(R₉)₂]ₙN(R₉)SO₂N(R)₂, [C(R₉)₂]ₙOSO₂R, [C(R₉)₂]ₙN(R₉)SO₂R, [C(R₉)₂]ₙSOₚR, [C(R₉)₂]ₙN(R₉)CSN(R)₂, [C(R₉)₂]ₙN(R₉)C(=NR₉)N(R)₂, [C(R₉)₂]ₙSO₂N(R)₂, [C(R₉)₂]ₙC(NR₉)N(R)₂, [C(R₉)₂]ₙCOR, O[C(R₉)₂]ₘOR, N(R)[C(R₉)₂]ₘOR, F, Cl, Br, CF₃, CN, or =O when Ar is Het;
R₄, R₅, and R₆ are independently H, a straight or branched alkyl of 1–6 carbons, a cycloalkyl of 3–6 carbons, [C(R₉)₂]ₙOR, [C(R₉)₂]ₙN(R)₂, F, Cl, Br, CN, CF₃, =O when Ar is Het; [C(R₉)₂]ₙN(R₉)COR, [C(R₉)₂]ₙSOₚR, [C(R₉)₂]ₙR, [C(R₉)₂]ₙ(O)COR, O[C(R₉)₂]ₘOR, N(R)[C(R₉)₂]ₘOR, [C(R₉)₂]ₙN(R₉)CON(R)₂, [C(R₉)₂]ₙ(O)CON(R)₂, [C(R₉)₂]ₙNR₉CO₂R, [C(R₉)₂]ₙCOR, [C(R₉)₂]ₙCO₂R, [C(R₉)₂]ₙCON(R)₂, [C(R₉)₂]ₙN(R₉)SO₂R, [C(R₉)₂]ₙSO₂N(R)₂, [C(R₉)₂]ₙN(R₉)SO₂OR, [C(R₉)₂]ₙOSO₂N(R)₂, [C(R₉)₂]ₙN(R₉)SO₂N(R)₂, [C(R₉)₂]ₙC(=NR₉)N(R)₂, [C(R₉)₂]ₙN(R₉)C(=NR₉)N(R)₂, [C(R₉)₂]ₙHet;
any two of R₁–R₃ or R₄–R₆ may together form a ring of 5–6 total atoms which may contain 0–3 heteroatoms;
X is NH, NR₈;
f is an integer of from 0 to 3;
n is an integer of from 0 to 3;
m is an integer of from 2 to 4;
p is an integer from 1 to 2;
R₇ is a straight or branched alkyl of 1–6 carbons or a carbocycle of 3–6 carbons;
R₈ is a straight or branched alkyl of 1–6 carbons, a carbocycle of 3–6 carbons, (CH₂)ₙPh, or a (CH₂)ₙheterocycle of 5–6 atoms containing 1–4 heteroatoms and wherein the (R)₂ in N(R)₂ optionally forms a heterocycle containing the nitrogen, all optionally substituted by F, Ci, Br, OR₉, CN, CO₂R₉, N(R₉)₂, NR₉COR₉, CF₃, or =O; or an alkyl group bearing polar functionalities, optionally including OH, NH₂, CN;
R₁ and R₈ may together form a ring of 5–6 atoms;
R is independently H, a straight or branched alkyl of 1–6 carbons, (CH₂)ₙPh, or a (CH₂)ₙheterocycle of 5–6 atoms containing 1–4 heteroatoms and wherein the (R)₂ in N(R)₂ optionally forms a heterocycle containing the nitrogen, all optionally substituted by F, Cl, Br, OR₉, CN, CO₂R₉, N(R₉)₂, NR₉COR₉, CF₃, or =O;
R₉ is independently H, a straight or branched alkyl of 1–4 carbons, or phenyl;
R₁₀ is independently H, a straight or branched alkyl of 1–4 carbons, F, Cl, Br, OR₉ or N(R₉)₂;
R₁, R₂, R₃, R₄, R₅, R₆, R₇, R₈, R₉ and R₁₀ may be alkene or alkyne of from 2 to 6 carbon atoms;

Ar₁ and Ar₂ are independently phenyl or Het;
Het is a heterocycle of from 5–6 atoms having from 1–4 heteroatoms or a fused heterocycle of from 9–10 atoms having 1–3 heteroatoms
wherein the heteroatoms are independently N, O or S,
A compound, which upon administering to mammals such as a human being converts into a compound according to Formula, I is within the scope of this invention.

DESCRIPTION OF PREFERRED EMBODIMENTS

The present invention is based in great part on the discovery of the inventors that novel 3-position Nitrogen substituted 6,6-disubstituted-5, 6-dihydropyrones and related compounds possess antiviral properties. The HIV protease activities of these compounds are not dependent on the pH of the environment in which they act. The binding affinities to HIV protease measured in vitro, at different pH mediums namely 4.7 and 6.2 were the same. The compounds possessing 3-position sulfur substituted 6,6-disubstituted-5, 6-dihydropyrones exhibited higher binding affinities at lower pH (namely 4.7) compared to higher pH (namely 6.2) of the assay medium ( Tummino, P. J.; Vara Prasad, J. V. N.; Ferguson, D.; Nouhan, C.; Graham, N.; Domagala, J.; Ellsworth, E.; Gajda, C.; Hagen, S. E.; Lunney, E. A.; Para, K. S.; Tait, B. D.; Pavlovlsky, A.; Erickson, J. W.; Gracheck, S.; McQuade, T. J.; Hupe, D. J. *BioOrganic and Medicinal Chemistry* 1996, 4(9), 1401–1410; Tait, B. D., Hagen, S., Domagala, J. M., Ellsworth, E., Gajda, C., Hamilton, H., Vara Prasad, J. V. N., Ferguson, D., Graham, N., Hupe, D., Nouhan, C., Tummino, P. J., Humblet, C., Lunney, E. A., Pavlovsky, A., Rubin, J., Baldwin, E. T., Bhat, T. N., Erickson, J. W., Gulnik, S. V., Liu, B. *J. Med. Chem.*, 1997, 40, 3781). (Table 1).

TABLE 1

| | IC₅₀s (μM) measured in vitro against HIV protease enzyme | |
|---|---|---|
| Compound | pH (4.7) | pH (6.2) |
| | 0.028 | 0.28 |
| | 0.010 | 0.035 |

TABLE 1-continued

| | IC$_{50}$s ($\mu$M) measured in vitro against HIV protease enzyme | |
|---|---|---|
| Compound | pH (4.7) | pH (6.2) |
| [structure] | 0.004 | 0.004 |

IC$_{50}$ indicates the concentration of the inhibitor at 50% inhibition.

The compounds of the present invention lacks chiral center at the 3-position of the 6, 6-disubstituted-5,6-dihydropyrones, unlike 3-position carbon containing 6,6-disubstituted-5, 6-dihydropyrones. (Upjohn's patents; Thaisrivongs, S.; Skulnick, H. I.; Turner, S. R.; Strobach, J. W.; Tommasi, R. A.; Johnson, P. D.; Aristoff, P. A.; Judge, T. M.; Gammill, R. B.; Morris, J. K.; Romines, K. R.; Chrusciel, R. A.; Hinshaw, R. R.; Chong, K.-T.; Tarpley, W. G.; Poppe, S. M.; Slade, D. E.; Lynn, J. C.; Horng, M.-M.; Tomich, P. K.; Seest, E. P.; Dolak, L. A.; Howe, W. J.; Howard, G. M.; Schwende, F. J.; Toth, L. N.; Padbury, G. E.; Wilson, K. F.; Rush, B. D.; Ruwart, M. J.; Koeplinger, K. A.; Zhao, Z.; Cole, S.; Zaya, R. M.; Kakuk, T. J.; Janakiraman, M. N.; Watenpaugh, K. D. *J. Med. Chem.*, 1996, 39, 5349). The lack of chiral centers at 3-position offers an obvious synthetic advantage. Thus these compounds are easy to synthesize compared to 3-position carbon containing 6,6-disubstituted-5, 6-dihydropyrones.

Moreover, the substituents at 6-position of the 6,6-disubstituted-3-nitrogen substituted-5, 6-dihydropyrones occupy different binding pockets of the HIV protease as revealed by X-ray crystal structure of compound 1 binding to HIV protease when compared to the similar substitutents present in 3-carbon substituted-6,6-disubstituted-5, 6-dihydropyrones (for example PNU-140690; Thaisrivongs, S.; Skulnick, H. I.; Turner, S. R.; Strobach, J. W.; Tommasi, R. A.; Johnson, P. D.; Aristoff, P. A.; Judge, T. M.; Gammill, R. B.; Morris, J. K.; Romines, K. R.; Chrusciel, R. A.; Hinshaw, R. R.; Chong, K.-T.; Tarpley, W. G.; Poppe, S. M.; Slade, D. E.; Lynn, J. C.; Horng, M.-M.; Tomich, P. K.; Seest, E. P.; Dolak, L. A.; Howe, W. J.; Howard, G. M.; Schwende, F. J.; Toth, L. N.; Padbury, G. E.; Wilson, K. F.; Rush, B. D.; Ruwart, M. J.; Koeplinger, K. A.; Zhao, Z.; Cole, S.; Zaya, R. M.; Kakuk, T. J.; Janakiraman, M. N.; Watenpaugh, K. D. *J. Med. Chem.*, 1996, 39, 5349). It is interesting to note that PNU-140690 contains n-propyl and phenethyl groups at the 6-position of the 5,6-dihydropyran-2-one ring, somewhat similar to Example 1. However, n-propyl and phenethyl groups in PNU-140690 occupy S$_2$ and S$_1$ pocket of the enzyme, respectively. This orientation contrasts with Example 1, wherein the small alkyl group (isopropyl) occupies the S$_1$ pocket of the enzyme and 4-substituted phenethyl group occupies S$_2$ pocket. This result clearly demonstrates that different enantiomers are most active in these two series of HIV PR inhibitor, despite the common core. The differences in these two series is shown in a schematic diagram below:

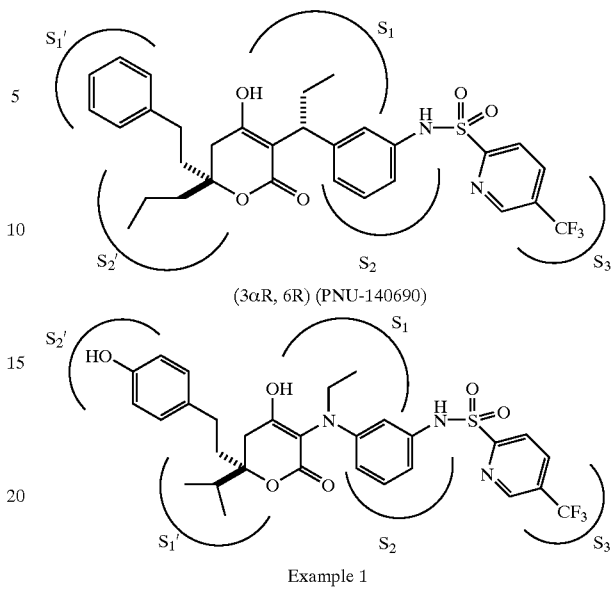

(3αR, 6R) (PNU-140690)

Example 1

These 3-position nitrogen substituted 5,6-dihydropyrones are expected to be extremely useful in the development of treatments for infections caused by viruses, especially by retroviruses that rely on aspartyl protease activities for replication and infectivity. One such retrovirus is HIV. For this reason, the antiviral 5,6-dihydropyrones are also expected to be very useful in the treatment of diseases and syndromes associates with viral pathogens. One such syndrome is AIDS.

Preferred compounds of Formula I are those wherein:

R$_1$ is isopropyl, iso-butyl, cyclopentyl, cyclohexyl or t-butyl;

R$_2$ is H, methyl, or ethyl;

R is H, a straight or branched alkyl of 1–4 carbons, (CH$_2$)$_n$Ph, or a (CH$_2$)$_n$heterocycle of 5–6 atoms containing 1–2 heteroatoms and wherein the (R)$_2$ in N(R)$_2$ may form a heterocycle containing the nitrogen, all optionally substituted by F, Cl, Br, OR$_9$, N(R$_9$)$_2$, N(R$_9$)COR$_9$, CF$_3$, or =O;

wherein Het is a heterocycle of from 5–6 atoms having 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of from 9–10 atoms having from 1–3 heteroatoms selected from: benzofuran, indole, benzothiophene, benzimidazole, benzthiazole, benzoxazole, quinoline, isoquinoline, cinnoline, quinazoline and quinoxaline.

X is NH.

Other preferred compounds of Formula I are those wherein:

R$_1$ is isopropyl or t-butyl;

R$_2$ is H, methyl or ethyl;

R$_3$ is H, (CH$_2$)$_n$OR, (CH$_2$)$_n$N(R)$_2$, (CH$_2$)$_n$N(R$_9$)COR, (CH$_2$)$_n$CON(R)$_2$, (CH$_2$)$_n$OC(O)N(R)$_2$, (CH$_2$)$_n$N(R$_9$)CON(R)$_2$, (CH$_2$)$_n$N(R$_9$)CO$_2$R, (CH$_2$)$_n$OSO$_2$N(R)$_2$, (CH$_2$)$_n$N(R$_9$)SO$_2$OR, (CH$_2$)$_n$N(R$_9$)SO$_2$N(R)$_2$, (CH$_2$)$_n$OSOR, (CH$_2$)$_n$N(R$_9$)SO$_2$R, (CH$_2$)$_n$SO$_2$R, (CH$_2$)$_n$N(R$_9$)C(S)N(R)$_2$, (CH$_2$)$_n$COR, O(CH$_2$)$_m$O(R$_9$), N(R)(CH$_2$)$_m$O(R$_9$), or C(CH$_3$)$_2$R$_9$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, CN, $CF_3$, =O, $(CH_2)_nN(R_9)COR$, $(CH_2)_nN(R_9)CON(R)_2$, $(CH_2)_nOC(O)N(R)_2$, $(CH_2)_nN(R_9)CO_2R$, $(CH_2)_nCOR$, $(CH_2)_nCON(R)_2$, $(CH_2)_nN(R_9)SO_2R$, $(CH_2)_nN(R_9)SO_2R$, $(CH_2)_nOSO_2N(R)_2$, or $R_4$ and $R_5$ may together form a ring of 5–6 total atoms which may contain 0–2 heteroatoms, R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle containing the nitrogen, all optionally substituted by F, Cl, Br, $OR_9$, $N(R_9)_2$, $N(R_9)COR_9$, or =O;

$R_8$ is an alkyl group of 1–5 carbons or a carbocycle of 3–6 atoms;

$Ar_1$ is a phenyl; and

Ar2 is phenyl or heterocycle of 5–6 atoms having from 14 heteroatoms.

Still other preferred compounds of Formula I are those wherein:

$R_3$ is H, $(CH_2)_nOR$, $(CH_2)_nN(R)_2$, $(CH_2)_nNR_9COR$, $(CH_2)_nCON(R)_2$, $(CH_2)_nOCON(R)_2$, $(CH_2)_nNR_9CON(R)_2$, $(CH_2)_nNR_9CO_2R$, $(CH_2)_nOSON(R)_2$, $(CH_2)_nNR_9SO_2OR$, $(CH_2)_nNR_9SO_2N(R)_2$, $(CH_2)_nOSO_2R$, $(CH_2)_nNR_9SO_2R$, $(CH_2)_nSO_2R$, $(CH_2)_nCOR$, $O(CH_2)_mOR$, $NR(CH_2)_mOR$, $C(CH_3)_2OR_9$, F, Cl, Br, $CF_3$, or =O when Ar is Het;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O when Ar is Het, $(CH_2)_pN(R_9)COR$, $(CH_2)_nN(R_9)CON(R)_2$, $(CH_2)_nOC(O)N(R)_2$, $(CH_2)_nN(R_9)CO_2R$, $(CH_2)_nCOR$, $(CH_2)_nC(O)N(R)_2$, $(CH_2)_nN(R_9)SO_2R$, $(CH_2)_nN(R_9)SO_2OR$, $(CH_2)_nOSON(R)_2$;

$R_1$ and $R_2$ or $R_4$ and $R_5$ may together form a ring of 5–6 total atoms, which may contain 0–2 heteroatoms;

$R_7$ is methyl, ethyl, isopropyl, cyclopropyl, cyclobutyl, cyclopentyl or cyclohexyl;

$R_8$ is a straight or branched alkyl of 1–5 carbons;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle containing the nitrogen, all optionally substituted by F, Cl, Br, $OR_9$, $N(R_9)_2$, $N(R_9)COR_9$, or =O;

Still other preferred compounds of Formula I are those wherein:

$R_3$ is H, $(CH_2)_nOR$, $(CH_2)_nN(R)_2$, $(CH_2)_nN(R_9)COR$, $(CH_2)_nC(O)N(R)_2$, $(CH_2)_nOCON(R)_2$, $(CH_2)_nN(R_9)CON(R)_2$, $(CH_2)_nN(R_9)CO_2R$, $(CH_2)_nOSO_2N(R)_2$, $(CH_2)_nN(R_9)SO_2OR$, $(CH_2)_nN(R_9)SO_2N(R)_2$, $(CH_2)_nOSOR$, $(CH_2)_nN(R_9)SO_2R$, $(CH_2)_nSO_2R$, $(CH_2)_nCOR$, $O(CH_2)_mOR_9$, $N(R)(CH_2)_mOR_9$, $C(CH_3)_2OR_9$, F, Cl, Br, $CF_3$, or =O when Ar is Het;

Any two of $R_1$–$R_3$ may together form a ring of 5–6 total atoms, which may contain 0–2 heteroatoms;

$R_1$ and $R_8$ may together form a ring to 5–6 atoms;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, $CF_3$, $(CH_2)_nN(R_9)COR$, $(CH_2)_nNR_9CON(R)_2$, $(CH_2)_nOC(O)N(R)_2$, $(CH_2)_nN(R_9)CO_2R$, $(CH_2)_nC(O)R$, $(CH_2)_nC(O)N(R)_2$, $(CH_2)_nN(R_9)SO_2R$, $(CH_2)_nNR_9SO_2OR$, $(CH_2)_nOSO_2N(R)_2$, $(CH_2)_n$Het;

any two of $R_4$–$R_6$ may together form a ring of 5–6 total atoms, which may contain 0–2 heteroatoms;

$R_8$ is a straight or branched alkyl of 1–5 carbons or a carbocycle of 3–6 atoms.

More preferred compounds of Formula I are those wherein:

$R_1$ is H;

$R_2$ is H;

$R_3$ is H, $(CH_2)_nOR$, $(CH_2)_nN(R)_2$, $(CH_2)_nOCON(R)_2$, $(CH_2)_nN(R_9)CON(R)_2$, $(CH_2)_nN(R_9)CO_2R$, $(CH_2)_nOSON(R)_2$, $(CH_2)_nN(R_9)SO_2OR$, $(CH_2)_nN(R_9)SO_2N(R)_2$, $(CH_2)_nN(R_9)SO_2R$, $(CH_2)_nSO_2R$, $O(CH_2)_mOR_9$, $N(R)(CH_2)_mOR_9$, or $C(CH_3)_2OR_9$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O when Ar is Het, $(CH_2)_nN(R_9)COR$, $(CH_2)_nN(R_9)C(O)N(R)_2$, $(CH_2)_nOC(O)N(R)_2$, $(CH_2)_nNR_9CO_2R$, $(CH_2)_nC(O)R$, $(CH_2)_nC(O)N(R)_2$, $(CH_2)_nN(R_9)SO_2R$, $(CH_2)_pN(R_9)SO_2OR$, $(CH_2)_pOSO_2N(R)_2$;

$R_4$ and $R_5$ may together form a ring of 5–6 total atoms, which may contain 0–2 heteroatoms;

$R_8$ is a straight or branched alkyl of 1–5 atoms or a carbocycle of 3–6 atoms;

R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may be a heterocycle containing the nitrogen, all optionally substituted by F, Cl, Br, $OR_9$, $N(R_9)_2$, $N(R_9)C(O)R_9$, or =O;

$R_1$ and $R_8$ may together form a ring of 5–6 atoms.

$Ar_1$ is phenyl; and

Ar2 is phenyl, furan, pyrrole, thiophene, oxazole, isoxazole, thiazole, pyrazole, tetrazole, or pyridine.

Other more preferred compounds of Formula I are those wherein:

$R_2$ is H;

$R_3$ is H, $(CH_2)_nOR$, $(CH_2)_nN(R)_2$, $(CH_2)_nN(R)COR$, $(CH_2)_nCON(R)_2$, $(CH_2)_nOC(O)N(R)_2$, $(CH_2)_nN(R_9)C(O)N(R)_2$, $(CH_2)_nN(R_9)CO_2R$, $(CH_2)_nOSON(R)_2$, $(CH_2)_nN(R_9)SO_2R$, $(CH_2)_nN(R_9)SO_2N(R)_2$, $(CH_2)_nOSO_2R$, $(CH_2)_nN(R_9)SO_2R$, $(CH_2)_nSO_2R$, $O(CH_2)_mOR$, $NR(CH_2)_mOR_9$, $C(CH_3)_2OR_9$, or =O when Ar is Het, $R_4$, $R_5$, and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O when Ar is Het, $(CH_2)_pN(R_9)COR$, $(CH_2)_pN(R_9)C(O)N(R)_2$, $(CH_2)_nOC(O)N(R)_2$, $(CH_2)_nN(R_9)CO_2R$, $(CH_2)_nCOR$, $(CH_2)_nCON(R)_2$, $(CH_2)_nN(R_9)SO_2R$, $(CH_2)_nN(R_9)SO_2OR$, $(CH_2)_nOSON(R)_2$;

$R_4$ and $R_5$ may together form a ring of 5–6 total atoms, which may contain 0–2 heteroatoms;

$R_8$ is ethyl, propyl, butyl;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle having nitrogen, all optionally substituted by F, Cl, Br, $OR_9$, $N(R_9)_2$, $NR_9CO(R_9)$, or =O;

$Ar_1$ is phenyl, thiophene, thiazole, pyridine, benzothiophene, benzthiazole, benzoxazole, quinoline or isoquinoline.

Still other more preferred compounds of formula I are those wherein:

$R_2$ is H;

$R_3$ is $CH_2OH$, $NH_2OCH_2CH_2OH$, NHCOR, $OSO_2N(R)_2$, $N(R_9)SO_2OR$, $N(R_9)SO_2R$, or $OSO_2R$;

$R_4$, $R_5$ and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O when Ar is Het, $(CH_2)_nNR_9COR$, $(CH_2)_nNR_9CON(R)_2$, $(CH_2)_nOCON(R)_2$, $(CH_2)_nNR_9CO_2R$, $(CH_2)_nCOR$, $(CH_2)_nCON(R)_2$, $(CH_2)_nNR_9SO_2R$, $(CH_2)_nNR_9SO_2OR$, $(CH_2)_nOSO_2N(R)_2$;

$R_4$ and $R_5$ may together form a ring of 5–6 total atoms, which may contain 0–2 heteroatoms;

R is H, a straight or branched alkyl of 1–4 carbons, $(CH_2)_n Ph$, or a $(CH_2)_n$heterocycle of 5–6 atoms having from 1–2 heteroatoms and wherein the $(R)_2$ in $N(R)_2$ may be a heterocycle having nitrogen, all optionally substituted by F, Cl, Br, $OR_9$, $N(R_9)_2$, $NR_9COR_9$, or =O;

$R_{10}$ is H, a straight or branched alkyl of from 1–4 carbons, F, Cl, Br, $OR_9$, or $N(R_9)_2$;

$Ar_1$ is phenyl; and

Ar2 is a heterocycle of 5–6 atoms having from 1–4 heteroatoms;

Still other more preferred compounds of Formula I are those wherein;

$R_1$ is H.;

$R_2$ is H;

$R_3$ is H, $(CH_2)_n OR$, $(CH_2)_n N(R)_2$, $(CH_2)_n N(R_9)COR$, $(CH_2)_n C(O)N(R)_2$, $(CH_2)_n OC(O)N(R)_2$, $(CH_2)_n N(R_9)C(O)N(R)$, $(CH_2)_n N(R_9)CO_2 R$, $(CH_2)_n OSON(R)_2$, $(CH_2)_n N(R_9)SO_2 OR$, $(CH_2)_n N(R_9)SO_2 N(R)_2$, $(CH_2)_n OSO_2 R$, $(CH_2)_n N(R_9)SO_2 R$, $(CH_2)_n SO_2 R$, $(CH_2)_n N(R_9)C(S)$ $N(R)_2$, $(CH_2)_n COR$, $O(CH_2)_m OR$, $NR(CH_2)_m OR_9$, $C(CH_3)_2 R_9$, F, Cl, Br, or =O when Ar is Het;

$R_4$, $R_5$ and $R_6$ are independently H, methyl, ethyl, OH, $CH_2 H$, $CH_2 CH_2 H$, F, Cl, $NH_2$;

any two $R_4$–$R_6$ may form a ring of 5–6 atoms having from 1–2 heteroatoms;

$R_8$ is ethyl, propyl, butyl;

R is H, a straight or branched alkyl of 1–4 carbons, $(CH_2)_n Ph$, or a $(CH_2)_n$heterocycle of 5–6 atoms having from 1–2 heteroatoms or a heterocycle having a nitrogen, all optionally substituted by F, Cl, Br, $OR_9$, $N(R_9)_2$, $NR_9 OR_9$ or =O;

$Ar_1$ is phenyl, furan, thiophene, thiazole, pyridine, imidazole, benzofuran, benzothiophene, benzimidazole, benzthiazole, quinoline, or isoquinoline; and $Ar_2$ is phenyl.

Still other more preferred compounds of formula I are those wherein:

$R_1$ is H or methyl;

$R_2$ is H or methyl;

$R_3$ is H, $(CH_2)_n OR$, $(CH_2)_n N(R)_2$, or =O;

$R_4$, $R_5$, and $R_6$ are independently H, methyl, OH, $CH_2 H$, $CH_2 CH_2 H$, $NH_2$ or F;

$R_7$ is H, isopropyl, butyl, sec-butyl, cyclobutyl, cyclopentyl, or cyclohexyl;

$R_8$ is ethyl, propyl, butyl;

R is H, methyl, ethyl, phenyl, or $CH_2 Ph$ and wherein the $(R)_2$ of $N(R)_2$ may be a heterocycle having a nitrogen;

$R_{10}$ is H, F, or $CH_3$;

$Ar_1$ is phenyl, furan, thiophene, thiazole, pyridine, imidazole, indole, benzofuran, benzothiophene, benzimidazole, benzthiazole, quinoline, or isoquinoline; and Ar2 is phenyl, furan, thiazole, pyridine, imidazole, indole, benzofuran, benzothiophene, benzimidazole, benzthiazole, quinoline, or isoquinoline.

Other preferred compounds of Formula I are those wherein:

$R_1$ is H or methyl;

$R_2$ is H or methyl;

$R_3$ is H, $NH_2 OH$, $CH_2 R$, $CH_2 N(R)_2$, $CH_2 CON(R)_2$, $CH_2 OSO_2 N(R)_2$, $CH_2 NHSO_2 R$, $CH_2 NHSO_2 R$, $CH_2 OSO_2 R$, Cl, Br, or $OCH_2 CH_2 H$;

$R_4$, $R_5$, and $R_6$ are independently H, methyl, ethyl, isopropyl, OH, $NH_2 CH_2 R$, $CH_2 N(R)_2$, =O, F, Cl, Br, or $CH_2 NRCOR$;

$R_7$ is methyl, ethyl, isopropyl, cyclopropyl, cyclobutyl, or cyclopentyl;

$R_8$ is ethyl, propyl, butyl;

R is H, methyl, ethyl, Ph, $CH_2 Ph$, and wherein the $(R)_2$ in $N(R)_2$ may be a heterocycle having a nitrogen;

$R_1$ and $R_8$ may together form a ring of 5–6 total atoms;

$R_{10}$ is H, F, or $CH_3$;

$Ar_1$ is phenyl, thiophene, thiazole, furan, pyridine, benzothiophene, benzofuran, benzthiazole, benzoxazole, indole, quinoline, or isoquinoline; and Ar2 is phenyl, furan, thiophene, oxazole, isoxazole, imidazole, thiazole, pyrazole, pyridine, benzofuran, benzothiophene, benzimidazole, benzthiazole, indole, quinoline, or isoquinoline; and f is an integer of 2.

Other preferred compounds of Formula I are those wherein:

$R_1$ is H;

$R_2$ is H;

$R_3$ is H, $NH_2 OH$, $CH_2 R$, $CH_2 N(R)_2$, $CH_2 CON(R)_2$, $OSO_2 N(R)_2$, $NHSO_2 OR$, $NHSO_2 R$, $OSO_2 R$, or $OCH_2 CH_2 H$;

$R_4$, $R_5$, and $R_6$ are independently H, methyl, ethyl, isopropyl, OH, $NH_2 CH_2 R$, $CH_2 N(R)_2$, =O when Ar is Het, F, Cl, Br, or $CH_2 NRCOR$;

$R_7$ is methyl, ethyl, n-propyl, isopropyl, cyclopropyl, cyclobutyl, or cyclopentyl;

$R_8$ is ethyl, propyl, butyl;

R is H, methyl, ethyl, Ph, $CH_2 Ph$, and wherein the $(R)_2$ in $N(R)_2$ may be a heterocycle containing the nitrogen;

$R_{10}$ is H, F, or $CH_3$;

$R_1$ and $R_8$ may together form a ring of 5–6 total atoms;

$Ar_1$ is phenyl, furan, thiophene, oxazole, isoxazole, imidazole, thiazole, pyrazole, pyridine, benzofuran, benzothiophene, benzimidazole, benzthiazole, indole, quinoline, or isoquinoline; and $Ar_2$ is phenyl, furan, thiophene, oxazole, isoxazole, imidazole, thiazole, pyrazole, pyridine, benzofuran, benzothiophene, benzimidazole, benzthiazole, indole, quinoline, or isoquinoline.

Still other preferred compounds of Formula I are those wherein:

$R_1$ is H;

$R_2$ is H;

$R_3$ is $NH_2 CH_2 H$, $OCH_2 CH_2 H$, $CH_2 CH_2 H$, or $NHSO_2 Ar_1$;

$R_4$, $R_5$, and $R_6$ are independently H, $NH_2 CH_2 H$, =O when Ar is Het, methyl, ethyl, or isopropyl;

$R_7$ is n-propyl, isopropyl or tert-butyl;

$R_8$ is ethyl, propyl or n-butyl;

$R_{10}$ is H, F, or $CH_3$;

$Ar_1$ is phenyl; and

Ar2 is phenyl, furan, thiophene, imidazole, thiazole, indole, pyrazole, or pyridine;

f is an integer of value 2.

Especially preferred compounds of the invention are:

5-Trifluoromethyl-pyridine-2-sulfonic acid {3-[(4-hydroxy-6-isopropyl-2-oxo-6-phenethyl-5,6-dihydro-2H-pyran-3-yl)-propyl-amino]-phenyl}-amide;

5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

5-Trifluoromethyl-pyridine-2-sulfonic acid {3-[ethyl-(4-hydroxy-6-isopropyl-2-oxo-6-phenethyl-5,6-dihydro-2H-pyran-3-yl)-amino]-phenyl}-amide;

5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl }-propyl-amino)-phenyl]-amide;

5-Trifluoromethyl-pyridine-2-sulfonic acid [3-(ethyl-{4-hydroxy-6-[2-(4-hydroxy-phenyl)-ethyl]-2-oxo-6-propyl-5,6-dihydro-2H-pyran-3-yl}-amino)-phenyl]-amide;

5-Trifluoromethyl-pyridine-2-sulfonic acid [3-(ethyl-{4-hydroxy-6-[2-(4-hydroxy-phenyl)-ethyl]-6-isopropyl-2-oxo-5,6-dihydro-2H-pyran-3-yl}-amino)-phenyl]-amide;

4-Hydroxy-6-[2-(4-hydroxy-phenyl)-ethyl]-6-isopropyl-3-(phenyl-propyl-amino)-5,6-dihydro-pyran-2-one;

6-Cyclopentyl-4-hydroxy-6-[2-(3-hydroxy-phenyl)-ethyl]-3-(phenyl-propyl-amino)-5, 6-dihydro-pyran-2-one;

4-Hydroxy-6-[2-(2-hydroxymethyl-phenyl)-ethyl]-6-isopropyl-3-(phenyl-propyl-amino)-5,6-dihydro-pyran-2-one;

Thiophene-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

5-Trifluoromethyl-pyridine-2-sulfonic acid [3-({4-hydroxy-6-(2-phenyethyl)-6-(n-propyl)-2-oxo-5,6-dihydro-2H-pyran-3-yl}-propyl-amino)-phenyl]-amide;

5-Trifluoromethyl-pyridine-2-sulfonic acid [3-({6-cyclopentyl-4-hydroxy-6-[2-(4-hydroxy-phenyl)-ethyl]-2-oxo-5,6-dihydro-2H-pyran-3-yl}-propyl-amino)-phenyl]-amide;

3-(Butyl-phenyl-amino)-4-hydroxy-6-[2-(4-hydroxy-phenyl)-ethyl]-6-isopropyl-5,6-dihydro-pyran-2-one;

Pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

3-(Butyl-phenyl-amino)-4-hydroxy-6-[2-(4-hydroxy-phenyl)-ethyl]-6-isopropyl-5,6-dihydro-pyran-2-one;

3-(Butyl-phenyl-amino)-6-cyclopentyl-4-hydroxy-6-[2-(3-hydroxy-phenyl)-ethyl]-5,6-dihydro-pyran-2-one;

5-Trifluoromethyl-pyridine-2-sulfonic acid [3-({6-[2-(4-amino-phenyl)-ethyl]-4-hydroxy-6-isopropyl-2-oxo-5,6-dihydro-2H-pyran-3-yl}-propyl-amino)-phenyl]-amide;

3-[(3,4-Dichloro-phenyl)-propyl-amino]-4-hydroxy-6-[2-(4-hydroxy-phenyl)-ethyl]-6-isopropyl-5,6-dihydro-pyran-2-one;

4-Hydroxy-3-[(3-hydroxymethyl-phenyl)-propyl-amino]-6-[2-(4-hydroxy-phenyl)-ethyl]-6-isopropyl-5,6-dihydro-pyran-2-one;

3-({4-Hydroxy-6-[2-(4-hydroxy-phenyl)-ethyl]-6-isopropyl-2-oxo-5,6-dihydro-2H-pyran-3-yl}-phenyl-amino)-propionitrile;

3-Diphenylamino-4-hydroxy-6-[2-(4-hydroxy-phenyl)-ethyl]-6-isopropyl-5,6-dihydro-pyran-2-one; and Pyridine-2-sulfonic acid {3-[ethyl-(4-hydroxy-6-isopropyl-2-oxo-6-phenethyl-5,6-dihydro-2H-pyran-3-yl)-amino]-phenyl}-amide.

The term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkylene or alkyne groups may contain one or more sites of unsaturation such as double or triple carbon-carbon bonds. The alkyl group is unsubstituted or substituted by from 1 to 3 substituents selected from F, Cl, Br, OH, $NH_2$, CN, $NO_2$, $OCH_3$, $OCH_2CH_2H$, $NHCH_3$, or $N(CH_3)_2$.

The term "cycloalkyl" means a hydrocarbon ring, which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NHR—, —$CO_2R$, —COR, aryl, or heteroaryl wherein alkyl (R), aryl, and heteroaryl are defined as herein.

The term "carbocycle" means cycloalkyl as defined above.

The term "heteroatoms" means a nitrogen, sulfur, or oxygen.

The term "heterocycle" means a heterocyclic radical which are 5–6 atoms having 1–4 heteroatoms and selected from 1–4 heteroatoms or a fused heterocycle of from 9–10 atoms having 1–3 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane, unsubstituted or substituted by 1 to 2 substituents selected from alkyl as defined above. For heterocycles containing sulfur, the oxidized sulfur heterocycles containing SO or $SO_2$ groups are also included.

The term "fused heterocycle" refers to a heterocycle that is adjoined as two consecutive positions with a phenyl ring or another heterocycle. such rings may include 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see for example, *Protective Groups in Organic Synthesis*, 2nd ed., T. W. Green and P. G. Wuts, John Wiley & Sons, New York, NY 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc.

Some of the compounds of Formula I are capable of further forming pharmaceutically acceptable acid-addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S.M., et al., "Pharmaceutical Salts," *Journal of Pharmaceutical Science,* 1977;66:1–19.

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof Configuration drawn is most preferred.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01-mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra. A number of general reactions such as oxidations and reductions are not shown in detail but can be done by methods understood by one skilled in the art. General transformations are well reviewed in "Comprehensive Organic Transformation" by Richard Larock, and the series "Compendium of Organic Synthetic Methods" (1989) published by Wiley-Interscience. In general, the starting materials were obtained from commercial sources unless otherwise indicated.

Synthesis of Compounds

There are two steps of the synthesis of desired products: 1) the preparation of diazocompounds from 6,6-disubstituted-5,6-dihydropyrones; 3) coupling of amines to diazo derivatives of 6,6-disubstituted-5,6-dihydropyrones to complete the preparation of the compounds of the invention (Scheme 1).

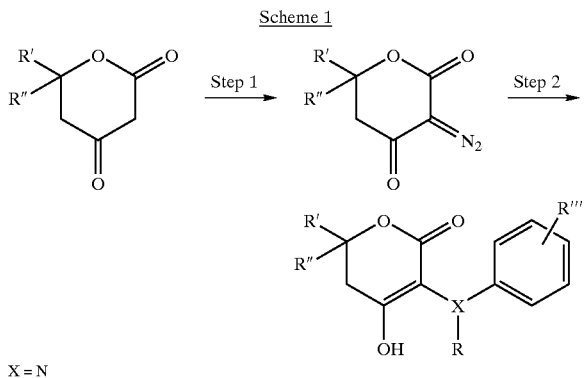

X = N

Preparation of 6,6-disubstituted-5,6-dihydropyrones

Racemic as well as enantiomerically pure 5,6-dihydropyrones were synthesized as described in U.S. patents referred to above.

Preparation of 3-diazo-6,6disubstituted-5,6-dihydropyrones (step 1)

To the 6,6-disubstituted-5,6-dihydropyrone (1 eq.) taken in a solvent like DMF was added sodium hydrogen phosphate (monobasic) (1–2 eq.), followed by (p-acetylamino)-phenylsulfonylazide (1–1.5 eq.). After stirring the reaction at room temperature for 3 to 16 hours. The reaction was quenched by adding a saturated aqueous solution of sodium hydrogen phosphate (dibasic) and diluted with ethyl acetate. Organic layer was separated and aqueous layer was extracted with ethyl acetate (3–4 times). Combined organic layer was dried over $MgSO_4$ and concentrated. The crude product was purified by flash silica gel chromatography to afford pure 3-diazo-6,6-disubstituted-5,6-dihydropyrones.

Coupling of amines to 3-diazo-6,6-disubstituted-5,6-dihydropyrones (step 2)

The 3-diazo-6,6-disubstituted-5,6-dihydropyrone (1 eq.) was dissolved in an aromatic hydrocarbon solvent like benzene or toluene. To this solution the amine (3–10 eq was added followed by rhodium (III) acetate dimer (0.01 to 0.2 eq.). The reaction was kept at 80° C. for 2 to 6 hours. The reaction mixture was cooled and diluted with ethyl acetate. The organic layer was washed with dilute hydrochloric acid, brine and dried over $MgSO_4$. Organic layer was concentrated and the crude product was purified by flash silica gel chromatography to afford the final product.

The amines used in the step 2 were either commercially available or prepared as described below:

Preparation of amines

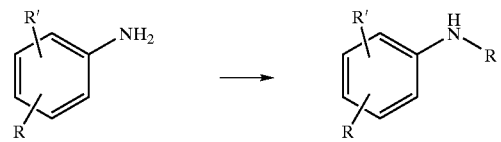

The amines, which can be used in Scheme 1, step 2; are prepared by reductive amination of the corresponding appropriately substituted anilines with aldehydes by a number of methods. One of the methods involve the use of reducing agents like sodium cyanoborohydride; whereas the other method involved the use of a heterogeneous catalysts like Raney nickel or Palladium on carbon under hydrogen atmosphere. Organic layer was concentrated and the crude product was purified by flash silica gel chromatography to afford the final product.

Preparation of Sulfonamides

Sulfonamides were prepared from the corresponding amines as follows:

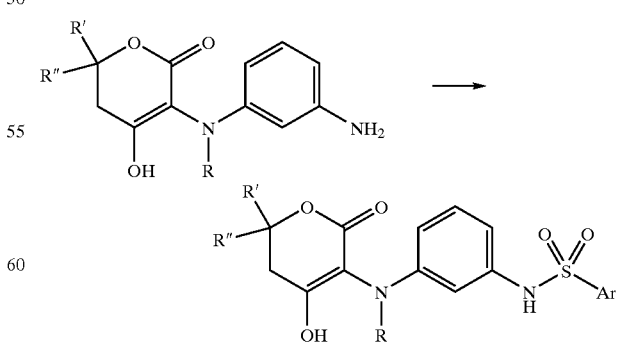

6,6-disubstituted-5,6-dihydropyrone (1 eq.) was taken in a halogenated solvent like dichlorometane. To this solution pyridine followed by sulfonyl chloride was added. The reaction was kept under stirring at room temperature for 6 to 18 hours. The reaction was quenched with dilute hydrochloric acid (1N) and diluted with ethyl acetate. The organic layer was separated; concentrated and the crude product was purified by flash silica gel chromatography to afford the final product.

TABLE A

Final Dihydropyrones

| Example | Ar₂ | Chirality at C-6 | Ar₁ | R₇ | X | Melting Point (°C.) | Mass Spe (APCI) |
|---|---|---|---|---|---|---|---|
| 1 | phenyl | S | 3-(N-(5-CF₃-pyridin-2-yl)sulfonamido)phenyl | Iso-propyl | N-(n-propyl) | | 618 (M + H) |
| 2 | 4-hydroxyphenyl | S | 3-(N-(5-CF₃-pyridin-2-yl)sulfonamido)phenyl | Iso-propyl | N-(n-propyl) | 107–110 | 634 (M + H) |
| 3 | phenyl | RS | 3-(N-(5-CF₃-pyridin-2-yl)sulfonamido)phenyl | Iso-propyl | N-(Ethyl) | | 604 (M + H) |
| 4 | 4-hydroxyphenyl | RS | 3-(N-(5-CF₃-pyridin-2-yl)sulfonamido)phenyl | Iso-propyl | N-(n-propyl) | | 634 (M + H) |
| 5 | 4-hydroxyphenyl | RS | 3-(N-(5-CF₃-pyridin-2-yl)sulfonamido)phenyl | n-propyl | N-(Ethyl) | | 620 (M + H) |
| 6 | 4-hydroxyphenyl | RS | 3-(N-(5-CF₃-pyridin-2-yl)sulfonamido)phenyl | Iso-propyl | N-(Ethyl) | | 620 (M + H) |
| 7 | 4-hydroxyphenyl | S | phenyl | Iso-propyl | N-(n-propyl) | 171–173 | 410 (M + H) |

TABLE A-continued

Final Dihydropyrones

| Example | Ar$_2$ | Chirality at C-6 | Ar$_1$ | R$_7$ | X | Melting Point (° C.) | Mass Spe (APCI) |
|---------|--------|------------------|--------|-------|---|----------------------|-----------------|
| 8 | 3-HO-phenyl | S | phenyl | Cyclopentyl | N-(n-propyl) | 74–76 | 436 (M + H) |
| 9 | 2-(HOCH$_2$)-phenyl | RS | phenyl | Iso-propyl | N-(n-propyl) | 58–60 | 425 (M + H) |
| 10 | 4-HO-phenyl | S | 3-(thiophene-2-sulfonylamino)phenyl | Iso-propyl | N-(n-propyl) | 85–87 | 571 (M + H) |
| 11 | phenyl | RS | 3-[(5-CF$_3$-pyridin-2-yl)sulfonylamino]phenyl | n-propyl | N-(Ethyl) | | 608 (M + H) |
| 12 | 4-HO-phenyl | RS | 3-[(5-CF$_3$-pyridin-2-yl)sulfonylamino]phenyl | Cyclopentyl | N-(n-propyl) | 104–106 | 660 (M + H) |
| 13 | 4-HO-phenyl | S | phenyl | Iso-propyl | N-(n-propyl) | 196–198 | 424 (M + H) |
| 14 | 4-HO-phenyl | RS | 3-(pyridin-2-ylsulfonylamino)phenyl | Iso-propyl | N-(n-propyl) | >122 | 575 (M + H) |
| 15 | 4-HO-phenyl | RS | phenyl | Iso-propyl | N-(n-propyl) | 69–71 | 424 (M + H) |

TABLE A-continued

Final Dihydropyrones

| Example | Ar₂ | Chirality at C-6 | Ar₁ | R₇ | X | Melting Point (° C.) | Mass Spe (APCI) |
|---|---|---|---|---|---|---|---|
| 16 | 3-HO-phenyl | S | phenyl | Cyclo-pentyl | N-(n-propyl) | 64–66 | 450 (M + H) |
| 17 | 4-H₂N-phenyl | RS | 3-[N-(5-CF₃-pyridin-2-yl)sulfonamido]phenyl | Iso-propyl | N-(n-propyl) | 170–172 | 633 (M + H) |
| 18 | 4-HO-phenyl | S | 3,4-dichlorophenyl | Iso-propyl | N-(n-propyl) | 188–191 | 479 (M + H) |
| 19 | 4-HO-phenyl | RS | 3-(hydroxymethyl)phenyl | Iso-propyl | N-(n-propyl) | 61–63 | 440 (M + H) |
| 20 | 4-H₂N-phenyl | RS | phenyl | Iso-propyl | N-(Phenyl) | 138–140 | 443 (M + H) |
| 21 | 4-HO-phenyl | RS | phenyl | Iso-propyl | N-(2-cyano ethyl) | 119–121 | 421 (M + H) |
| 22 | 4-HO-phenyl | RS | phenyl | Iso-propyl | N-(Phenyl) | 83–85 | 444 (M + H) |
| 23 | phenyl | RS | 3-[N-(pyridin-2-yl)sulfonamido]phenyl | Iso-propyl | N-(Ethyl) | | 536 (M + H) |

TABLE A-continued

Final Dihydropyrones

| Example | Ar₂ | Chirality at C-6 | Ar₁ | R₇ | X | Melting Point (° C.) | Mass Spe (APCI) |
|---|---|---|---|---|---|---|---|
| 24 | phenyl | S | phenyl | Iso-propyl | N-(n-propyl) | 147–149 | 395 (M + H) |
| 25 | 4-hydroxyphenyl | S | 3-(methoxycarbonyl)phenyl | Iso-propyl | N-(n-propyl) | 96–98 | 468 (M + H) |
| 26 | phenyl | RS | 3,5-dichlorophenyl | Iso-propyl | N-(n-propyl) | 86–88 | 478, 480 (M + H) |
| 27 | 4-aminophenyl | RS | phenyl | Iso-propyl | N-(n-propyl) | 91–96 | 417 (M + H) |
| 28 | phenyl | RS | phenyl | Iso-propyl | N-(n-propyl) | 160–162 | 394 (M + H) |
| 29 | 4-hydroxyphenyl | RS | phenyl | Iso-propyl | N-(n-propyl) | 186–188 | 411 (M + H) |
| 30 | 3-thienyl | RS | phenyl | Iso-propyl | N-(n-propyl) | 53–55 | 400 (M + H) |
| 31 | 4-hydroxyphenyl | RS | phenyl | Cyclo-pentyl | N-(n-propyl) | 95 | 436 (M + H) |

TABLE A-continued

Final Dihydropyrones

| Example | Ar₂ | Chirality at C-6 | Ar₁ | R₇ | X | Melting Point (° C.) | Mass Spe (APCI) |
|---|---|---|---|---|---|---|---|
| 32 | 4-HO-phenyl | S | 3-(HOCH₂)-phenyl | Iso-propyl | N-(n-propyl) | 71–73 | 440 (M + H) |
| 33 | 4-HO-phenyl | RS | phenyl | Iso-propyl | N-(Ethyl) | 63–65 | 396 (M + H) |
| 34 | 3-HO-phenyl | S | phenyl | Cyclo-pentyl | N-(Phenyl) | 90–92 | 470 (M + H) |
| 35 | 4-HO-phenyl | RS | phenyl | Iso-propyl | N-(Cyclo-hexyl) | 104–106 | 450 (M + H) |
| 36 | 4-HO-phenyl | RS | phenyl | Iso-propyl | N-(Cyclo-pentyl) | 83–85 | 436 (M + H) |
| 37 | phenyl | S | 3-(thiophene-2-sulfonamido)-phenyl | Iso-propyl | N-(n propyl) | | 555 (M + H) |
| 38 | 4-HO-phenyl | RS | 4-methoxy-phenyl | Iso-propyl | N-(Phenyl) | 95–96 | 474 (M + H) |
| 39 | 4-HO-phenyl | RS | phenyl | Methyl | N-(n-propyl) | 179–181 | 382 (M + H) |

TABLE A-continued

Final Dihydropyrones

| Example | Ar₂ | Chirality at C-6 | Ar₁ | R₇ | X | Melting Point (°C.) | Mass Spe (APCI) |
|---|---|---|---|---|---|---|---|
| 40 | HO-phenyl | RS | 3-HO-phenyl | Iso-propyl | N-(Phenyl) | 95–97 | 460 (M + H) |
| 41 | HO-phenyl | RS | phenyl | n-butyl | N-(n-propyl) | 58–60 | 424 (M + H) |
| 42 | HO-phenyl | RS | phenyl | Cyclo-propyl | N-(n-propyl) | 74–75 | 408 (M + H) |
| 43 | HO-phenyl | RS | 3-Cl-phenyl | Iso-propyl | N-(Iso-propyl) | 75–77 | 410 (M + H) |
| 44 | phenyl | RS | 3-(1-methylimidazole-5-sulfonamido)phenyl | n-propyl | N-(Ethyl) | | 539 (M + H) |
| 45 | HO-phenyl | S | 4-methylphenyl | Iso-propyl | N-(Ethyl) | 166–169 | 411 (M + H) |
| 46 | HO-phenyl | RS | 3-(4-cyanobenzenesulfonamido)phenyl | methyl | N-(n-propyl) | 125–128 | 591 (M + H) |
| 47 | HO-phenyl | RS | phenyl | Iso-propyl | N-(2-hydroxyethyl) | 85–86 | 412 (M + H) |

TABLE A-continued

Final Dihydropyrones

| Example | Ar$_2$ | Chirality at C-6 | Ar$_1$ | R$_7$ | X | Melting Point (° C.) | Mass Spe (APCI) |
|---------|--------|------------------|--------|-------|---|----------------------|-----------------|
| 48 | 1H-pyrazol-3-yl | RS | phenyl | Isopropyl | N-(n-propyl) | 85–89 | 418 (M + H) |
| 49 | benzo[1,3]dioxol-5-yl | RS | phenyl | Iso-propyl | N-(n-propyl) | 93–95 | 438 (M + H) |
| 50 | 4-hydroxyphenyl | RS | 3-methylphenyl | methyl | N-(n-propyl) | 144–146 | 397 (M + H) |
| 51 | 4-hydroxyphenyl | RS | 3-[(1-methyl-1H-imidazol-5-yl)sulfonylamino]phenyl | n-propyl | N-(Ethyl) |  | 555 (M + H) |
| 52 | 4-hydroxyphenyl | RS | phenyl | Iso-propyl | N-(Iso-pentyl) | 70–72 | 438 (M + H) |
| 53 | 4-hydroxyphenyl | RS | phenyl | Iso-propyl | N-(Cyclo-propyl) | 102–104 | 408 (M + H) |
| 54 | 4-hydroxyphenyl | RS | phenyl | Iso-propyl | N-(Tert-butyl) |  | 425 (M + H) |
| 55 | 5-hydroxypyridin-2-yl | S | 4-fluorophenyl | Iso-propyl | N-(Iso-propyl) |  | 428 (M + H) |

TABLE A-continued

Final Dihydropyrones

| Example | Ar₂ | Chirality at C-6 | Ar₁ | R₇ | X | Melting Point (° C.) | Mass Spe (APCI) |
|---------|-----|------------------|-----|-----|---|---------------------|-----------------|
| 56 | phenyl | RS | 3-aminophenyl | Iso-propyl | N-(Ethyl) | | 395 (M + H) |
| 57 | 4-hydroxyphenyl | RS | 5-hydroxynaphth-1-yl | Iso-propyl | N-(n-propyl) | 93–96 | 476 (M + H) |
| 58 | 4-hydroxyphenyl | S | 2-methylphenyl | Iso-propyl | N-(Ethyl) | | 410 (M + H) |
| 59 | 4-hydroxyphenyl | RS | naphth-2-yl | Iso-propyl | N-(Ethyl) | 97–99 | 446 (M + H) |
| 60 | 4-hydroxyphenyl | RS | naphth-1-yl | Iso-propyl | N-(Ethyl) | 86–88 | 446 (M + H) |
| 61 | 4-hydroxyphenyl | RS | benzyl | Iso-propyl | N-(Phenyl) | 75–77 | 458 (M + H) |
| 62 | 4-hydroxyphenyl | RS | 3-(N,N-dimethylsulfamoyloxy)phenyl | Methyl | N-(n-propyl) | 58–60 | 506 (M + H) |

TABLE A-continued

Final Dihydropyrones

| Example | Ar₂ | Chirality at C-6 | Ar₁ | R₇ | X | Melting Point (° C.) | Mass Spe (APCI) |
|---|---|---|---|---|---|---|---|
| 63 | 4-HO-phenyl | RS | 2-(propyl-NH-)phenyl | methyl | — | 188–190 | 400 (M + H) |
| 64 | phenyl | RS | 2-isopropyl-phenyl | Phenyl | NH | 69–73 | 429 (M + H) |
| 65 | phenyl | RS | 2-tert-butyl-phenyl (with additional substituent) | Phenyl | NH | 99–101 | 462 (M + H) |

The Table above shows the compounds of the invention as racemic; however, the R and S forms are within the scope of the invention. The S form is the preferred.

The compound names corresponding to Examples 1-65 in Table above are:

(1) 5-Trifluoromethyl-pyridine-2-sulfonic acid {3-[(4-hydroxy-6-isopropyl-2-oxo-6-phenethyl-5,6-dihydro-2H-pyran-3-yl)-propyl-amino]-phenyl }-amide;
(2) 5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl }-propyl-amino)-phenyl]-amide;
(3) 5-Trifluoromethyl-pyridine-2-sulfonic acid {3-[ethyl-(4-hydroxy-6-isopropyl-2-oxo-6-phenethyl-5,6-dihydro-2H-pyran-3-yl)-amino]-phenyl}-amide;
(4) 5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;
(5) 5-Trifluoromethyl-pyridine-2-sulfonic acid [3-(ethyl-{4-hydroxy-6-[2-(4-hydroxy-phenyl)-ethyl]-2-oxo-6-propyl-5,6-dihydro-2H-pyran-3-yl}-amino)-phenyl]-amide;
(6) 5-Trifluoromethyl-pyridine-2-sulfonic acid [3-(ethyl-{4-hydroxy-6-[2-(4-hydroxy-phenyl)-ethyl]-6-isopropyl-2-oxo-5,6-dihydro-2H-pyran-3-yl }-amino)-phenyl]-amide;
(7) 4-Hydroxy-6-[2-(4-hydroxy-phenyl)-ethyl]-6-isopropyl-3-(phenyl-propyl-amino)-5,6-dihydro-pyran-2-one;
(8) 6-Cyclopentyl-4-hydroxy-6-[2-(3-hydroxy-phenyl)-ethyl]-3-(phenyl-propyl-amino)-5,6-dihydro-pyran-2-one;
(9) 4-Hydroxy-6-[2-(2-hydroxymethyl-phenyl)-ethyl]-6-isopropyl-3-(phenyl-propyl-amino)-5,6-dihydro-pyran-2-one;
(10) Thiophene-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;
(11) 5-Trifluoromethyl-pyridine-2-sulfonic acid [3-({4-hydroxy-6-[2-(phenethyl)-6-(n-propyl)-2-oxo-5,6-dihydro-2H-pyran-3-yl}-propyl-amino)-phenyl]-amide;
(12) 5-Trifluoromethyl-pyridine-2-sulfonic acid [3-({6-cyclopentyl-4-hydroxy-6-[2-(4-hydroxy-phenyl)-ethyl]-2-oxo-5,6-dihydro-2H-pyran-3-yl}-propyl-amino)-phenyl]-amide;
(13) 3-(Butyl-phenyl-amino)-4-hydroxy-6-[2-(4-hydroxy-phenyl)-ethyl]-6-isopropyl-5,6-dihydro-pyran-2-one;
(14) Pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;
(15) 3-(Butyl-phenyl-amino)-4-hydroxy-6-[2-(4-hydroxy-phenyl)-ethyl]-6-isopropyl-5,6-dihydro-pyran-2-one;
(16) 3-(Butyl-phenyl-amino)-6-cyclopentyl-4-hydroxy-6-[2-(3-hydroxy-phenyl)-ethyl]-5,6-dihydro-pyran-2-one;
(17) 5-Trifluoromethyl-pyridine-2-sulfonic acid [3-({6-[2-(4-amino-phenyl)-ethyl]-4-hydroxy-6-isopropyl-2-oxo-5,6-dihydro-2H-pyran-3-yl}-propyl-amino)-phenyl]-amide;

(18) 3-[(3,4-Dichloro-phenyl)-propyl-amino]-4-hydroxy-6-[2-(4-hydroxy-phenyl)-ethyl]-6-isopropyl-5,6-dihydro-pyran-2-one;
(19) 4-Hydroxy-3-[(3-hydroxymethyl-phenyl)-propyl-amino]-6-[2-(4-hydroxy-phenyl)-ethyl]-6-isopropyl-5,6-dihydro-pyran-2-one;
(20) [2-(4-Amino-phenyl)-ehtyl]-dihenylamino-hydroxy-isopropyl-5,6-dihydro-pyran-2-on;
(21) 3-({4-Hydroxy-6-[2-(4-hydroxy-phenyl)-ethyl]-6-isopropyl-2-oxo-5,6-dihydro-2H-pyran-3-yl }-phenyl-amino)-propionitrile;
(22) 3-Diphenylamino-4-hydroxy-6-[2-(4-hydroxy-phenyl)-ethyl]-6-isopropyl-5,6-dihydro-pyran-2-one;
(23) Pyridine-2-sulfonic acid {3-[ethyl-(4-hydroxy-6-isopropyl-2-oxo-6-phenethyl-5,6-dihydro-2H-pyran-3-yl)-amino]-phenyl }-amide;
(24) 4-Hydroxy-6-isopropyl-6-phenethyl-3-(phenyl-propyl-amino)-5,6-dihydro-pyran-2-one;
(25) 3-({4-Hydroxy-6-[2-(4-hydroxy-phenyl)-ethyl]-6-isopropyl-2-oxo-5,6-dihydro-2H-pyran-3-yl}-propyl-amino)-benzoic acid methyl ester;
(26) 3-[(3,5-Dichloro-phenyl)-propyl-amino]-4-hydroxy-6-[2-(4-hydroxy-phenyl)-ethyl]-6-isopropyl-5,6-dihydro-pyran-2-one;
(27)-6-[2-(4-Amino-phenyl)-ethyl]-4-hydroxy-6-isopropyl-3-(phenyl-propyl-amino)-5,6-dihydro-pyran-2-one;
(28) 4-Hydroxy-6-isopropyl-6-phenethyl-3-(phenyl-propyl-amino)-5,6-dihydro-pyran-2-one;
(29) 4-Hydroxy-6-[2-(4-hydroxy-phenyl)-ethyl]-6-isopropyl-3-(phenyl-propyl-amino)-5,6-dihydro-pyran-2-one;
(30) 4-Hydroxy-6-isopropyl-3-(phenyl-propyl-amino)-6-(2-thiophen-3-yl-ethyl)-5,6-dihydro-pyran-2-one;
(31) 6-Cyclopentyl-4-hydroxy-6-[2-(4-hydroxy-phenyl)-ethyl]-3-(phenyl-propyl-amino)-5,6-dihydro-pyran-2-one,
(32) 4-Hydroxy-3-[(3-hydroxymethyl-phenyl)-propyl-amino]-6-[2-(4-hydroxy-phenyl)-ethyl]-6-isopropyl-5,6-dihydro-pyran-2-one;
(33) 3-(Ethyl-phenyl-amino)-4-hydroxy-6-[2-(4-hydroxy-phenyl)-ethyl]-6-isopropyl-5,6-dihydro-pyran-2-one;
(34) 6-Cyclopentyl-3-diphenylamino-4-hydroxy-6-[2-(3-hydroxy-phenyl)-ethyl]-5,6-dihydro-pyran-2-one;
(35) 3-(Cyclohexyl-phenyl-amino)-4-hydroxy-6-[2-(4-hydroxy-phenyl)-ethyl]-6-isopropyl-5,6-dihydro-pyran-2-one;
(36) 3-(Cyclopentyl-phenyl-amino)-4-hydroxy-6-[2-(4-hydroxy-phenyl)-ethyl]-6-isopropyl-5,6-dihydro-pyran-2-one;
(37) Thiophene-2-sulfonic acid {3-[(4-hydroxy-6-isopropyl-2-oxo-6-phenethyl-5,6-dihydro-2H-pyran-3-yl)-propyl-amino]-phenyl }-amide;
(38) 4-Hydroxy-6-[2-(4-hydroxy-phenyl)-ethyl]-6-isopropyl-3-[(4-methoxy-phenyl) -phenyl-amino]-5,6-dihydro-pyran-2-one;
(39) 4-Hydroxy-6-[2-(4-hydroxy-phenyl)-ethyl]-6-methyl-3-(phenyl-propyl-amino)-5,6-dihydro-pyran-2-one;
(40) 4-Hydroxy-6-[2-(4-hydroxy-phenyl)-ethyl]-3-[(3-hydroxy-phenyl)-phenyl-amino]-6-isopropyl-5,6-dihydro-pyran-2-one;
(41) 6-Butyl-4-hydroxy-6-[2-(4-hydroxy-phenyl)-ethyl]-3-(phenyl-propyl-amino)-5,6-dihydro-pyran-2-one;
(42) 6-Cyclopropyl-4-hydroxy-6-[2-(4-hydroxy-phenyl)-ethyl]-3-(phenyl-propyl-amino)-5,6-dihydro-pyran-2-one;
(43) 4-Hydroxy-6-[2-(4-hydroxy-phenyl)-ethyl]-6-isopropyl-3-(isopropyl-phenyl-amino)-5,6-dihydro-pyran-2-one;
(44) 1-Methyl-1H-imidazole-4-sulfonic acid {3-[ethyl-(4-hydroxy-2-oxo-6-phenethyl-6-propyl-5,6-dihydro-2H-pyran-3-yl)-amino]-phenyl }-amide;
(45) 3-(Ethyl-p-tolyl-amino)-4-hydroxy-6-[2-(4-hydroxy-phenyl)-ethyl]-6-isopropyl-5,6-dihydro-pyran-2-one;
(46) 4-Cyano-N-[3-({4-hydroxy-6-[2-(4-hydroxy-phenyl)-ethyl]-6-methyl-2-oxo-5,6-dihydro-2H-pyran-3-yl }-propyl-amino)-phenyl]-benzenesulfonamide;
(47) 4-Hydroxy-3-[(2-hydroxy-ethyl)-phenyl-amino]-6-[2-(4-hydroxy-phenyl)-ethyl]-6-isopropyl-5,6-dihydro-pyran-2-one;
(48) 4-Hydroxy-6-isopropyl-3-(phenyl-propyl-amino)-6-[2-(1H-pyrazol-3-yl)-ethyl]-5,6-dihydro-pyran-2-one;
(49) 6-(2-Benzo[1,3]dioxol-5-yl-ethyl)-4-hydroxy-6-isopropyl-3-(phenyl-propyl-amino)-5,6-dihydro-pyran-2-one;
(50) 4-Hydroxy-6-[2-(4-hydroxy-phenyl)-ethyl]-6-methyl-3-(propyl-m-tolyl-amino)-5,6-dihydro-pyran-2-one;
(51) 1-Methyl-1H-imidazole-4-sulfonic acid [3-(ethyl-{4-hydroxy-6-[2-(4-hydroxy-phenyl)-ethyl]-2-oxo-6-propyl-5,6-dihydro-2H-pyran-3-yl }-amino)-phenyl]-amide;
(52) 4-Hydroxy-6-[2-(4-hydroxy-phenyl)-ethyl]-6-isopropyl-3-[(3-methyl-butyl) -phenyl-amino]-5,6-dihydro-pyran-2-one;
(53) 3-(Cyclopropyl-phenyl-amino)-4-hydroxy-6-[2-(4-hydroxy-phenyl)-ethyl]-6-isopropyl-5,6-dihydro-pyran-2-one;
(54) 3-(tert-Butyl-phenyl-amino)4-hydroxy-6-[2-(4-hydroxy-phenyl)-ethyl]-6-isopropyl-5,6-dihydro-pyran-2-one;
(55) (S)-3-[(4-Fluoro-phenyl)-isopropyl-amino]-4-hydroxy-6-[2-(4-hydroxy-phenyl)-ethyl]-6-isopropyl-5,6-dihydro-pyran-2-one;
(56) 3-[(3-Amino-phenyl)-ethyl-amino]-4-hydroxy-6-isopropyl-6-phenethyl-5,6-dihydro-pyran-2-one;
(57) 4-Hydroxy-3-[(5-hydroxy-naphthalen-1-yl)-propyl-amino]-6-[2-(4-hydroxy-phenyl)-ethyl]-6-isopropyl-5,6-dihydro-pyran-2-one;
(58) 3-(Ethyl-o-tolyl-amino)-4-hydroxy-6-[2-(4-hydroxy-phenyl)-ethyl]-6-isopropyl-5,6-dihydro-pyran-2-one;
(59) 3-(Ethyl-naphthalen-2-yl-amino)-4-hydroxy-6-[2-(4-hydroxy-phenyl)-ethyl]-6-isopropyl-5,6-dihydro-pyran-2-one;
(60) 3-(Ethyl-naphthalen-1-yl-amino)-4-hydroxy-6-[2-(4-hydroxy-phenyl)-ethyl]-6-isopropyl-5,6-dihydro-pyran-2-one;
(61) 3-(Benzyl-phenyl-amino)-4-hydroxy-6-[2-(4-hydroxy-phenyl)-ethyl]-6-isopropyl-5,6-dihydro-pyran-2-one;
(62) Dimethyl-sulfamic acid 3-({4-hydroxy-6-[2-(4-hydroxy-phenyl)-ethyl]-6-methyl-2-oxo-5,6-dihydro-2H-pyran-3-yl }-propyl-amino)-phenyl ester;
(63) 3-(3,4-Dihydro-2H-quinoxalin-1-yl)-4-hydroxy-6-[2-(4-hydroxy-phenyl)-ethyl]-6-methyl-5,6-dihydro-pyran-2-one;
(64) 4-Hydroxy-3-(2-isopropylphenylamino)-6-phenethyl-6-phenyl-5,6-dihydro-pyran-2-one;
(65) 3-(2-tert-Butyl-5-methyl)-phenylamino)-4-hydroxy-6-phenethyl-6-phenyl-5,6-dihydro-pyran-2-one;

The following sections provide the experimental methodology for the in vitro and in vivo assays employed to demonstrate the efficacy and advantages of the compounds of the current invention.

The compounds of the present invention were evaluated for their in vitro inhibition of HIV protease and for their antiviral efficacy in HIV infected lymphocytes and the results shown in Table 2.

HIV Protease Assay

Materials

Recombinant HIV-1 protease (>96% purity) and HIV protease substrate III (the undecapeptide H-His-Lys-Ala- Arg-Val-Leu-Nph-Glu-Ala-Nle-Ser-NH$_2$, 97% purity) were purchased from Bachem Bioscience, Inc. (King of Prussia, Pa.).

Method

The methods employed follow the procedures of Tummino, et al., *Archives of Biochemistry and Biophysics*, 1995;316:523). For determination of Ki values, HIV-1 protease, 6.0 nM final concentration, was added to a solution containing inhibitor, 40 µM substrate III and 1.0% Me$_2$SO in assay buffer: 80 mM MES [2-(N-morpholine)ethane sufonic acid] hydrate, 160 mM NaCl, 1.0 mM EDTA (ethylenediaminetetraacetic acid) 0.1% polyethylene glycol (MW 8000) pH 6.2 at 37° C. (total volume, 100 & 1). Polyethylene glycol was used in the assay in place of glycerol since the former was reported to be a more effective stabilizing agent in the protease (Jordan, et al., *J. Biol. Chem.*, 1992;267:20028). The final inhibitor concentrations used were 0 (0.1, 0.2, in some experiments), 0.5, 1, 2, 5, 10, 20, 50, and 100 µM. The solution was mixed, incubated for 5 minutes and the reaction quenched by addition of trifluoracetic acid, 2% final. The (leu-p-nitro-phe) bond of the substrate is cleaved by the enzyme and substrate and products separated by reverse-phase HPLC (high pressure liquid chromatography). Absorbance was measured at 220 nm, peak areas determined, and percentage conversion to product used to calculate percentage control (=[% conversion (+inhibitor)/% conversion (−inhibitor)]×100).

Cellular Infection Assay

Compounds were tested in lymphocyte derived CEM cells using the XTT cytopathic procedures and were performed at Southern Research Institute (Buckheit, et al., *Antiviral Res.*, 1993;21:247; see also Weislow, et al., *J. Nat. Cancer Inst.*, 1989;81:577). Compound concentrations were 0.32, 1, 3.2, 10, 32, and 100 µM. The EC$_{50}$ represents the concentration of agent, which reduces HIV cytopathic effects 50% relative to untreated control. Cellular toxicity of the agents are estimated from the TC$_{50}$ which represents the concentration of the agent which inhibits 50% of the viability of uninfected cells.

Table 1 contains the results of the HIV protease assay Ki and the antiviral efficacy (EC$_{50}$, TC$_{50}$, TI) screening, where TI is the therapeutic index (TC$_{50}$/EC$_{50}$).

EC$_{50}$ indicates the concentration of the drug which provide 50% protection against HIV.

TC$_{50}$ indicates the concentration of the drug which elicits cytotoxicity in 50% of uninfected cells.

Ki means inhibitory constant; it approximately the equilibrium binding constant for the binding of the inhibitor to the free enzyme.

TABLE 1

Inhibition of HIV-Protease and Antiviral Efficacy in a CEM Cell Infection Assay

| Example | Protease Ki (nM) | EC$_{50}$ (µM) | TC$_{50}$ (µM) | TI |
|---|---|---|---|---|
| 1 | 0.029 | 0.7 | 63 | 90 |
| 2 | 0.083 | 1 | 71 | 71 |
| 3 | 0.96 | 1.1 | 66 | 60 |
| 4 | 0.01 | 1.1 | 84 | 76.4 |
| 5 | 0.17 | 1.3 | 113 | 86.9 |

TABLE 1-continued

Inhibition of HIV-Protease and Antiviral Efficacy in a CEM Cell Infection Assay

| Example | Protease Ki (nM) | EC$_{50}$ (µM) | TC$_{50}$ (µM) | TI |
|---|---|---|---|---|
| 6 | 0.44 | 1.3 | 133 | 102.3 |
| 7 | 0.13 | 1.3 | 200 | 153.8 |
| 8 | 0.35 | 1.3 | 67 | 51.5 |
| 9 | 2 | 1.4 | 101 | 72.1 |
| 13 | 0.2 | 1.5 | 156 | 104 |
| 14 | 0.54 | 1.6 | 210 | 131 |
| 21 | 1.6 | 2.7 | 320 | 118.5 |

Table 1 indicates that the compounds of the present invention have good to excellent activity toward inhibiting the HIV protease enzyme (Ki's) as well as activity in HIV infected cells, protecting the cells from HIV pathogenicity at µM and sub-µM concentrations.

While the forms of the invention herein disclosed constitute presently preferred embodiments, many others are possible. It is not intended herein to mention all of the possible equivalent forms or ramifications of the invention. It is understood that the terms used herein are merely descriptive, rather than limiting, and that various changes may be made without departing from the spirit or scope of the invention.

What is claimed is:

1. A compound of Formula I or its pharmaceutically acceptable salts

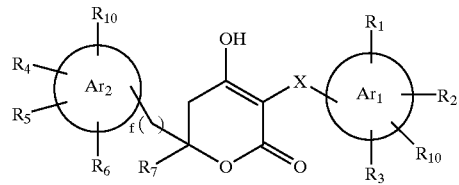

wherein:

R$_1$ is H, a straight or branched alkyl of 1–6 carbons or a carbocycle of 3–6 carbons;

R$_2$ is H, a straight or branched alkyl of 1–5 carbons or a carbocycle of 3–6 carbons;

R$_3$ is H, [C(R$_9$)$_2$]$_n$OR, [C(R$_9$)$_2$]$_n$N(R)$_2$, [C(R$_9$)$_2$]$_n$N (R$_9$) COR, [C(R$_9$)$_2$]$_n$CO$_2$R, [C(R$_9$)$_2$]$_n$(O)COR, [C(R$_9$)$_2$]$_n$CON(R)$_2$, [C(R$_9$)$_2$]$_n$OC(O)N(R)$_2$, [C(R$_9$)$_2$R], [C(R$_9$)$_2$]$_n$N(R$_9$)CON(R)$_2$, [C(R$_9$)$_2$]$_n$N(R$_9$)CO$_2$R, [C(R$_9$)$_2$]$_n$OSO$_2$N(R)$_2$, [C(R$_9$)$_2$]$_n$N(R$_9$)SO$_2$R, [C(R$_9$)$_2$]$_n$N(R$_9$)SO$_2$N(R)$_2$, [C(R$_9$)$_2$]$_n$OSO$_2$R, [C(R$_9$)$_2$]$_n$N (R$_9$)SO$_2$R, [C(R$_9$)$_2$]$_n$SO$_p$R, [C(R$_9$)$_2$]$_n$N (R$_9$)CSN(R)$_2$, [C(R$_9$)$_2$]$_n$N(R$_9$)C(=NR$_9$)N(R)$_2$, [C(R$_9$)$_2$]$_n$SO$_2$N(R)$_2$, [C(R$_9$)$_2$]$_n$C(NR$_9$)N(R)$_2$, [C(R$_9$)$_2$]$_m$COR, O[C(R$_9$)$_2$]$_m$OR, N(R)[C(R$_9$)$_2$]$_m$OR, F, Cl, Br, CF$_3$, CN, or =O when Ar is Het;

R$_4$, R$_5$, and R$_6$ are independently H, a straight or branched alkyl of 1–6 carbons, a cycloalkyl of 3–6 carbons, [C(R$_9$)$_2$]$_n$OR, [C(R$_9$)$_2$]$_n$N(R)$_2$, F, Cl, Br, CN, CF$_3$, =O when Ar is Het; [C(R$_9$)$_2$]$_n$N(R$_9$)COR, [C(R$_9$)$_2$]$_n$SO$_p$R, [C(R$_9$) $_2$]$_n$R, [C(R$_9$)$_2$]$_n$(O)COR, O[C(R$_9$)$_2$]$_m$OR, N(R) [C(R$_9$)$_2$]$_m$OR, [C(R$_9$)$_2$]$_n$N(R$_9$)CON(R)$_2$, [C(R$_9$)2]$_n$(O) CON(R)$_2$, [C(R$_9$)$_2$]$_n$NR$_9$CO$_2$R, [C(R$_9$)$_2$]$_n$COR [C(R$_9$)$_2$]$_n$CO$_2$R, [C(R$_9$)$_2$]$_n$CON(R)$_2$, [C(R$_9$)$_2$]$_n$N(R$_9$) SO$_2$R, [C(R$_9$)$_2$]$_n$SO$_2$N(R)$_2$, [C(R$_9$)$_2$]$_n$N(R$_9$)SO$_2$OR,

[C(R$_9$) $_2$]$_n$OSO$_2$N(R)$_2$, [C(R$_9$)$_2$]$_n$N(R$_9$)SO$_2$N(R)$_2$, [C(R$_9$)$_2$]$_n$C(=NR$_9$)N(R)$_2$, [C(R$_9$)$_2$]$_n$N(R$_9$)C(=NR$_9$)N(R)$_2$, [C(R$_9$)$_2$]$_n$Het;

or any 2 of R$_1$–R$_3$ or R$_4$–R$_6$ may together form a ring of 5–6 total atoms which may contain 0–3 heteroatoms;

X is NH or NR$_8$;

f is an integer of from 0 to 3;

n is an integer of from 0 to 3;

m is an integer of from 2 to 4;

p is an integer from 1 to 2;

R$_7$ is a straight or branched alkyl of 1–6 carbons or a carbocycle of 3–6 carbons;

R$_8$ is a straight or branched alkyl of 1–6 carbons, a carbocycle of 3–6 carbons, (CH$_2$)$_n$Ph, or a heterocycle of 5–6 atoms having 1–4 heteroatoms or a fused heterocycle of from 9–10 atoms having 1–3 heteroatoms all optionally substituted by F, Cl, Br, OR$_9$, CN, CO$_2$R$_9$, N(R$_9$)$_2$, NR$_9$COR$_9$, CF$_3$, or =O; or an alkyl group bearing an OH, NH$_2$, CN substituent;

or R$_1$ and R$_8$ may together form a carbocycle;

R is independently H, a straight or branched alkyl of 1–6 carbons, (CH$_2$)$_n$Ph, or a (CH$_2$)$_n$heterocycle of 5–6 atoms containing 1–4 heteroatoms, all optionally substituted by F, Cl, Br, OR$_9$, CN, CO$_2$R$_9$, N(R$_9$)$_2$, NR$_9$COR$_9$, CF$_3$, or =O;

R$_9$ is independently H, a straight or branched alkyl of 1–4 carbons, or phenyl;

R$_{10}$ is independently H, a straight or branched alkyl of 1–4 carbons, F, Cl, Br, OR$_9$ or N(R$_9$)$_2$; or R$_1$, R$_2$, R$_3$, R$_4$, R$_5$, R$_6$, R$_7$, R$_8$, R$_9$ and R$_{10}$ may be alkene or alkyne of from 2–6 carbon atoms;

Ar$_1$ and Ar$_2$ are independently phenyl;

provided that X is NR$_8$ when R$_7$ is a carbocycle.

2. A compound according to claim 1 wherein:

R$_1$ is H or a straight or branched alkyl of from 1 to 4 carbons or a carbocycle of from 3 to 5 carbons and;

R$_2$ is H or straight or branched alkyl of from 1 to 3 carbons; and

R$_8$ is H or straight or branched alkyl of from 1 to 6 carbons.

3. A compound according to claim 1 wherein:

R$_1$ is H or a straight or branched alkyl of from 1–4 carbons or a carbocycle of 3–5 carbons;

R$_2$ is H or a straight or branched alkyl of from 1–4 carbons or carbocycle of 3–5 carbons;

R$_3$ is H, [C(R$_9$)$_2$]$_n$OR, [C(R$_9$)$_2$]$_n$N(R)$_2$, [C(R$_9$)$_2$]$_n$N (R$_9$) COR, [C(R$_9$)$_2$]$_n$CO$_2$R, [C(R$_9$)$_n$(O)C(O)R, [C(R$_9$)]$_n$CON(R)$_2$, [C(R$_9$)$_n$OC(O)N(R)$_2$, [C(R$_9$)]$_{2n}$N (R$_9$)CON(R)$_2$, [C(R$_9$)$_2$]$_n$N(R$_9$)CO$_2$R, [C(R$_9$)$_2$]$_n$OSO$_2$N(R)$_2$, [C(R$_9$)$_2$]$_n$N(R$_9$)SO$_2$OR, [C(R$_9$)$_{2n}$N(R$_9$)SO$_2$N(R)$_2$, [C(R$_9$) $_2$]$_n$OSO$_2$R, [C(R$_9$) 2]$_n$N (R$_9$)SO$_2$R, [C(R$_9$)$_2$]$_n$SO$_p$R, [C(R$_9$)$_2$]$_n$N (R$_9$)C(S)N(R)$_2$, [C(R$_9$)$_2$]$_n$COR, O[C(R$_9$)$_2$]$_m$OR, N(R)[C(R$_9$)$_2$]$_m$OR, F, Cl, Br, CF$_3$, CN, or =O when Ar is Het;

R$_4$, R$_5$, and R$_6$ are independently H, a straight or branched alkyl of 1–6 carbons, a cycloalkyl of 3–6 carbons, [C(R$_9$)$_2$]$_n$OR, [C(H$_2$)$_2$]$_n$N(R)$_2$, F, Cl, Br, CN, CF$_3$, =O when Ar is Het; [C(R$_9$)$_2$]$_n$N(R$_9$)COR, [C(R$_9$)$_2$]$_n$SO$_n$R, [C(R$_9$)$_2$]$_n$N(R$_9$)C(O)N(R)$_2$, [C(R$_9$)$_2$]$_n$OCON(R)$_2$, [C(R$_9$)$_2$]$_n$NR$_9$CO$_2$R, [C(R$_9$)$_2$]$_n$COR, [C(R$_9$)$_2$]$_n$CO$_2$R, [C(R$_9$)$_2$]$_n$CON(R)$_2$, [C(R$_9$)$_2$]$_n$N (R$_9$)SO$_2$R, [C(R$_9$)$_2$]$_n$OSO$_2$N(R)$_2$ [C(R$_9$)$_2$]$_n$N(R$_9$)SO$_2$OR, [C(R$_9$)$_2$]$_n$ OSO$_2$NR$_2$, [C(R$_9$)$_2$]$_n$ Het;

or any two of R$_1$–R$_3$ or R$_4$–R$_6$ may together form a ring of 5–6 total atoms which may contain 0–2 heteroatoms;

Ar$_1$ is phenyl; and

Ar$_2$ is 4-hydroxylphenyl or phenyl.

4. A compound according to claim 1 wherein:

R$_1$ is independently H or a straight or branched alkyl of from 1–4 carbons or a carbocycle of 3–5 carbon atoms;

R$_2$ is independently H or a straight or branched alkyl of from 1–4 carbons or a carbocycle of 3–5 carbon atoms;

R$_3$ is independently H, (CH$_2$)$_n$OR, (CH$_2$)$_n$N(R)$_2$, (CH$_2$)$_n$N(R$_9$)COR, (CH$_2$)$_n$C(O)N(R)$_2$, (CH$_2$)$_n$OCON(R)$_2$, (CH$_2$)$_n$N(R$_9$)C(O)N(R)$_2$, (CH$_2$)$_n$N(R$_9$)CO$_2$R, (CH$_2$)$_n$OSO$_2$N(R)$_2$, (CH$_2$)$_n$NR$_9$SO$_2$OR, (CH$_2$)$_n$N(R$_9$)SO$_2$N(R)$_2$, (CH$_2$)$_n$OSO$_2$R, (CH$_2$)$_n$N(R$_9$)SO$_2$R, (CH$_2$)$_n$SO$_2$R, (CH$_2$)$_n$N(R$_9$)C(S)N(R)$_2$, (CH$_2$)$_n$COR, O(CH$_2$)$_m$OR$_9$, NR(CH$_2$)$_m$O(R$_9$), or C(CH$_3$)$_2$OR$_9$;

R$_4$, R$_5$, and R$_6$ are independently H, a straight or branched alkyl of 1–6 carbons, a cycloalkyl of 3–6 carbons, (CH$_2$)$_n$OR, (CH$_2$)$_n$N(R)$_2$, F, Cl, Br, CN, CF$_3$, =O, when Ar is Het; (CH$_2$)$_n$N(R$_9$)COR, (CH$_2$)$_n$N(R$_9$)C(O)N(R)$_2$, (CH$_2$)$_n$OC(O)N(R)$_2$, (CH$_2$)$_n$N(R$_9$)CO$_2$R, (CH$_2$)$_n$COR, (CH$_2$)$_p$C(O)N(R)$_2$, (CH$_2$)$_n$N(R$_9$)SO$_2$R, (CH$_2$)$_n$N(R$_9$)SO$_2$OR, (CH$_2$)$_n$OSO$_2$N(R)$_2$ wherein n is 0–2, or R$_4$ and R$_5$ may together form a ring of 5–6 total atoms which may contain 0–2 heteroatoms;

R is H, a straight or branched alkyl of 1–4 carbons, (CH$_2$)$_n$Ph, or a heterocycle of 5–6 atoms having 1–4 heteroatoms or a fused heterocycle of from 9–10 atoms having 1–3 heteroatoms, all optionally substituted by F, Cl, Br, OR$_9$, N(R$_9$)$_2$, NR$_9$COR$_9$, or =O;

Ar$_1$ is phenyl; and

Ar$_2$ is 4-hydroxyphenyl or phenyl.

5. A compound according to claim 1 wherein:

R$_3$ is H, (CH$_2$)$_n$OR, (CH$_2$)$_n$N(R)$_2$, (CH$_2$)$_n$N(R$_9$)COR, (CH$_2$)$_n$C(O)N(R) $_2$, (CH$_2$)$_n$OC(O)N(R)$_2$, (CH$_2$)$_n$N(R$_9$)C(O)N(R)$_2$, (CH$_2$)$_n$N(R$_9$)CO$_2$R, (CH$_2$)$_n$OSO$_2$N(R)$_2$, (CH$_2$)$_n$N(R$_9$)SO$_2$OR, (CH$_2$)$_n$N(R$_9$)SO$_2$N(R)$_2$, (CH$_2$)$_n$OSO$_2$R, (CH$_2$)$_n$N(R$_9$)SO$_2$R, (CH$_2$)$_n$SO$_2$R, (CH$_2$)$_n$COR, O (CH$_2$)$_m$OR, NR(CH$_2$)$_m$OR, C(CH$_3$)$_2$OR$_9$, F, Cl, Br, CF$_3$, or =O which is Het;

R$_4$, R$_5$, and R$_6$ are independently H, a straight or branched alkyl of 1–6 carbons, a cycloalkyl of 3–6 carbons, (CH$_2$)$_n$OR, (CH$_2$)$_n$N(R)$_2$, F, Cl, Br, =O, (CF$_2$)$_n$N(R$_9$) COR, (CH$_2$)$_n$N(R$_9$)C(O)N(R)$_2$, (CH$_2$)$_n$OC(O)N(R)$_2$, (CH$_2$)$_n$N(R)$_9$CO$_2$R, (CH$_2$)$_n$COR, (CH$_2$)$_n$C(O)N(R)$_2$, (CH$_2$)$_n$N(R)SO$_2$R, (CH$_2$)$_n$N(R$_9$)SO$_2$OR, (CH$_2$)$_n$OSO$_2$N(R)$_2$, wherein n is 0–2;

R$_4$ and R$_5$ may together form a ring of 5–6 total atoms, which may contain 0–2 heteroatoms;

R$_7$ is independently methyl, ethyl, isopropyl, cyclopropyl, cyclobutyl, cyclopentyl or cyclohexyl;

R$_8$ is independently H or a straight or branched alkyl of 1–6 carbons or a carbocycle of 3–6 carbons;

R is independently H, a straight or branched alkyl of 1–4 carbons, (CH$_2$)$_n$Ph, or a heterocycle of 5–6 atoms having 1–4 heteroatoms or a fused heterocycle of from 9–10 atoms having 1–3 heteroatoms, all optionally substituted by F, Cl, Br, OR$_9$, N(R$_9$)$_2$, NR$_9$COR$_9$, or =O;

Ar$_1$ is phenyl; and

Ar$_2$ is 4-hydroxylphenyl or phenyl.

6. A compound according to claim 1 wherein:

R$_1$ is H, or a straight or branched alkyl of 1–4 carbons or a carbocycle of 3–5 carbons;

$R_2$ is H or methyl or a straight or branched alkyl of 1–4 carbons or a carbocycle of 3–4 carbons;

$R_3$ is H, $(CH_2)_nOR$, $(CH_2)_nN(R)_2$, $(CH_2)_nN(R_9)COR$, $(CH_2)_nC(O)N(R)_2$, $(CH_2)_nOC(O)N(R)_2$, $(CH_2)_nN(R_9)C(O)N(R)_2$, $(CH_2)_nN(R_9)CO_2R$, $(CH_2)_nOSO_2N(R)_2$, $(CH_2)_nN(R_9)SO_2OR$, $(CH_2)_nN(R_9)SO_2N(R)_2$, $(CH_2)_nOSO_2R$, $(CH_2)_nN(R_9)SO_2R$, $(CH_2)_nSO_2R$, $(CH_2)_nCOR$, $O(CH_2)_mO(R_9)$, $NR(CH_2)_mOR_9$, $C(CH_3)_2OR_9$, F, Cl, Br, or $CF_3$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, $CF_3$, $(CH_2)_pN(R_9)C(O)R$, $(CH_2)_pN(R_9)C(O)N(R)_2$, $(CH_2)_pOC(O)N(R)_2$, $(CH_2)_nN(R_9)CO_2R$, $(CH_2)_nCOR$, $(CH_2)_nCON(R)_2$, $(CH_2)_nN(R_9)SO_2R$, $(CH_2)_nN(R_9)SO_2OR$, $(CH_2)_nOSO_2N(R)_2$, $(CH_2)_n$ Het wherein n is 0–2;

any two of $R_4$–$R_6$ may together form a ring of 5–6 total atoms, which may contain 0–2 heteroatoms;

X is $NR_8$;

R is H, a straight or branched alkyl of 1–4 carbons, $(CH_2)_nPh$, or a heterocycle of 5–6 atoms having 1–4 heteroatoms or a fused heterocycle of from 9–10 atoms having 1–3 heteroatoms, all optionally substituted by F, Cl, Br, $O(R_9)$, $N(R_9)_2$, $NR_9COR_9$, or =O;

$Ar_1$ is phenyl;

$Ar_2$ is 4hydroxyphenyl or phenyl; and $R_8$ and $R_1$ may together form a ring of 2–5 carbons.

7. A compound according to claim 1 wherein:

$R_1$ is H, or straight or branched alkyl of 1–4 carbons or a carbocycle of 3–5 carbons;

$R_2$ is H or a straight or branched alkyl of 1–4 carbons or a carbocycle of 3–5 carbons;

$R_3$ is H, $(CH_2)_nOR$, $(CH_2)_nN(R)_2$, $(CH_2)_nOC(O)N(R)_2$, $(CH_2)_nN(R_9)C(O)N(R)_2$, $(CH_2)_nN(R_9)CO_2R$, $(CH_2)_nOSO_2N(R)_2$, $(CH_2)_nN(R_9)SO_2OR$, $(CH_2)_nN(R_9)SO_2N(R)_2$, $(CH_2)_nN(R_9)SO_2R$, $(CH_2)_nSO_2R$, $O(CH_2)_mOR_9$, $NR(CH_2)_mOR_9$, or $C(CH_3)_2OR_9$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O, $(CH_2)_nN(R_9)C(O)R$, $(CH_2)_nN(R_9)C(O)N(R)_2$, $(CH_2)_nOC(O)N(R)_2$, $(CH_2)_nN(R_9)CO_2R$, $(CH_2)_nCOR$, $(CH_2)_nC(O)N(R)_2$, $(CH_2)_nN(R_9)SO_2R$, $(CH_2)_nN(R_9)SO_2OR$, $(CH_2)_nOSO_2N(R)_2$, wherein n is 0–2;

$R_4$ and $R_5$ may together form a ring of 5–6 total atoms, which may contain 0–2 heteroatoms;

R is H, a straight or branched alkyl of 1–4 carbons, $(CH_2)_nPh$, or a heterocycle of 5–6 atoms having 1–4 heteroatoms or a fused heterocycle of from 9–10 atoms having 1–3 heteroatoms, all optionally substituted by F, Cl, Br, $OR_9$, $N(R_9)_2$, $N(R_9)COR_9$, or =O;

$Ar_1$ is phenyl; and $Ar_2$ is phenyl or 4-hydroxyphenyl.

8. A compound according to claim 1 wherein:

$R_1$ is independently H, a straight or branched alkyl of 1–6 carbons or a carbocycle of 3–6 carbons;

$R_2$ is independently H, or a straight or branched alkyl of 1–6 carbons or a carbocycle of 3–6 carbons;

$R_3$ is independently H, $(CH_2)_nOR$, $(CH_2)_nN(R)_2$, $(CH_2)_nN(R)C(O)R$, $(CH_2)_nC(O)N(R)_2$, $(CH_2)_nOCON(R)_2$, $(CH_2)_nN(R_9)C(O)N(R)_2$, $(CH_2)_nN(R_9)CO_2R$, $(CH_2)_nOSO_2N(R)_2$, $(CH_2)_nN(R_9)SO_2OR$, $(CH_2)_nN(R_9)SO_2N(R)_2$, $(CH_2)_nOSO_2R$, $(CH_2)_nN(R_9)SO_2R$, $(CH_2)_nSO_2R$, $O(CH_2)_mOR$, $NR(CH_2)_mOR$, $C(CH_3)_2OR_9$, or =O when Ar is Het;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O, when Ar is Het, $(CH_2)_pN(R_9)COR$, $(CH_2)_pN(R_9)CON(R)_2$, $(CH_2)_pOC(O)N(R)_2$, $(CH_2)_nN(R_9)CO_2R$, $(CH_2)_nCOR$, $(CH_2)_nCON(R)_2$, $(CH_2)_nN(R_9)SO_2R$, $(CH_2)_nN(R_9)SO_2OR$, $(CH_2)_nOSO_2N(R)_2$, wherein n is 0–2;

$R_4$ and $R_5$ may together form a ring of 5–6 total atoms, which may contain 0–2 heteroatoms;

R is H, a straight or branched alkyl of 1–4 carbons, $(CH_2)_nPh$, or a heterocycle of 5–6 atoms having 1–4 heteroatoms or a fused heterocycle of from 9–10 atoms having 1–3 heteroatoms, all optionally substituted by F, Cl, Br, $O(R_9)$, $N(R_9)_2$, $NR_9COR_9$, or =O;

$Ar_1$ is phenyl; and $Ar_2$ is 4-hydroxyphenyl or phenyl.

9. A compound according to claim 1 wherein:

$R_1$ is independently H or straight or branched alkyl of 1–4 carbons or a carbocycle of 3–5 carbons;

$R_2$ is independently H or straight or branched alkyl of 1–4 carbons or a carbocycle of 3–5 carbons;

$R_3$ is independently $CH_2OH$, $NH_2$, $OCH_2CH_2OH$, NHCOR, $OSO_2N(R)_2$, $N(R_9)SO_2OR$, $NR_9SO_2R$, or $OSO_2R$;

$R_4$, $R_5$, and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O, $(CH_2)_nN(R_9)C(O)R$, $(CH_2)_nN(R_9)C(O)N(R)_2$, $(CH_2)_nOC(O)N(R)_2$, $(CH_2)_pN(R_9)CO_2R$; $(CH_2)_nCOR$, $(CH_2)_nC(O)N(R)_2$, $(CH_2)_nN(R_9)SO_2R$, $(CH_2)_nN(R_9)SO_2OR$, $(CH_2)_nOSO_2N(R)_2$, wherein n is 0–2;

$R_4$ and $R_5$ may together form a ring of 5–6 total atoms, which may contain 0–2 heteroatoms;

$R_7$ is independently a straight or branched alkyl of 1–6 carbons or a carbocycle of 3–6 carbons, $R_8$ is H;

R is independently H, a straight or branched alkyl of 1–4 carbons, $(CH_2)_nPh$, or a heterocycle of 5–6 atoms having 1–4 heteroatoms or a fused heterocycle of from 9–10 atoms having 1–3 heteroatoms and wherein the $(R)_2$ in $N(R)_2$ may be a heterocycle having nitrogen, all optionally substituted by F, Cl, Br, $OR_9$, $N(R_9)_2$, $N(R_9)C(O)R_9$, or =O;

$Ar_1$ and $Ar_2$ are phenyl.

10. A compound according to claim 1 wherein:

$R_1$ is H or straight or branched alkyl of 1–4 carbons or a carbocycle of 3–5 carbons;

$R_2$ is independently H or straight or branched alkyl of 1–4 carbons or a carbocycle of 3–5 carbons;

$R_3$ is independently H, $(CH_2)_nOR$, $(CH_2)_nN(R)_2$, $(CH_2)_nN(R_9)C(O)R$, $(CH_2)_nC(O)N(R)_2$, $(CH_2)_nOC(O)N(R)_2$, $(CH_2)_nN(R_9)C(O)N(R)$, $(CH_2)_nN(R_9)CO_2R$, $(CH_2)_nOSO_2N(R)_2$, $(CH_2)_nN(R_9)SO_2OR$, $(CH_2)_nN(R_9)SO_2N(R)_2(CH_2)_nOSO_2R$, $(CH_2)_nN(R_9)SO_2R$, $(CH_2)_nSO_2R$, $(CH_2)_nN(R_9)C(S)N(R)_2$, $(CH_2)_nCOR$, $O(CH_2)_mOR$, $NR(CH_2)_mOR_9$, $C(CH_3)_2OR_9$, F, Cl, Br, or =O when Ar is Het;

$R_4$, $R_5$ and $R_6$ are independently H, methyl, ethyl, OH, $CH_2OH$, $CH_2CH_2OH$, F, Cl, $NH_2$;

any two $R_4$–$R_6$ may form a ring of 5–6 atoms having from 1–2 heteroatoms;

X is $NR_8$;

R is independently H, a straight or branched alkyl of 1–4 carbons, $(CH_2)_nPh$, or a $(CH_2)_n$ heterocycle of 5–6 atoms having 1–4 heteroatoms or a fused heterocycle of from 9–10 atoms having 1–3 heteroatoms or a heterocycle having a nitrogen, all optionally substituted by F, Cl, Br, OR', $N(R')_2$, $N(R_9)COR_9$, or =O;

$R_8$ is a straight or branched alkyl of 1–4 carbons or a carbocycle of 3–5 carbon atoms;

$Ar_1$ and $Ar_2$ are phenyl.

11. A compound according to claim 1 wherein:

$R_1$ is independently H or straight or branched alkyl of 1–4 carbons or a carbocycle of 3–5 carbon atoms;

$R_2$ is independently H or branched alkyl of 1–4 carbons or a carbocycle of 3–5 carbon atoms;

$R_3$ is independently H, $(CH_2)_nOR$, $(CH_2)_nN(R)_2$, or =O when Ar is Het;

$R_4$, $R_5$, and $R_6$ are independently H, methyl, OH, $CH_2OH$, $CH_2CH_2OH$, $NH_2$, or F;

$R_7$ is independently H, isopropyl, butyl, sec-butyl, cyclobutyl, cyclopentyl, or cyclohexyl;

X is $NR_8$;

$R_8$ is independently H, ethyl, n-propyl or n-butyl;

R is independently H, methyl, ethyl, phenyl, or $CH_2Ph$ and wherein the $(R)_2$ of $N(R)_2$ may be a heterocycle having a nitrogen;

$R_{10}$ is independently H, F, or $CH_3$;

$Ar_1$ is phenyl; and $Ar_2$ is independently phenyl or 4-hydroxyphenyl.

12. A compound according to claim 1 wherein:

$R_1$ is independently H or straight or branched alkyl of 1–4 carbons or a carbocycle of 3–5 carbons;

$R_2$ is independently H or straight or branched alkyl of 1–4 carbons or a carbocycle of 3–5 carbons;

$R_3$ is independently H, $NH_2$, OH, $CH_2OR$, $CH_2N(R)_2$, $CH_2C(O)N(R)_2$, $CH_2OSO_2N(R)_2$, $CH_2NHSO_2N(R)_2$, $CH_2NHSO_2R$, $CH_2OSO_2R$, Cl, Br, or $OCH_2CH_2OH$;

$R_4$, $R_5$, and $R_6$ are independently H, methyl, ethyl, isopropyl, OH, $NH_2$, $CH_2OR$, $CH_2N(R)_2$, =O when Ar is Het, F, Cl, Br, or $CH_2N(R)C(O)R$;

$R_7$ is independently methyl, ethyl, isopropyl, cyclopropyl, cyclobutyl, or cyclopentyl;

X is $NR_8$;

$R_8$ is independently H, ethyl, n-propyl or n-butyl;

R is independently H, methyl, ethyl, Ph or $CH_2Ph$;

$R_{10}$ is independently H, F, or $CH_3$; and $Ar_1$ and $Ar_2$ are phenyl.

13. A compound according to claim 1 wherein:

$R_1$ is independently H or straight or branched alkyl of 1–4 carbons or a carbocycle of 3–5 carbon atoms;

$R_2$ is independently H or straight or branched alkyl of 1–4 carbons or a carbocycle of 3–5 carbon atoms;

$R_3$ is independently H, $NH_2$, OH, $CH_2OR$, $CH_2N(R)_2$, $CH_2C(O)N(R)_2$, $OSO_2N(R)_2$, $NHSO_2OR$, $NHSO_2R$, $OSO_2R$, or $OCH_2CH_2OH$;

$R_4$, $R_5$, and $R_6$ are independently H, methyl, ethyl, isopropyl, OH, $NH_2$, $CH_2OR$, $CH_2N(R)_2$, =O when Ar is Het, F, Cl, Br, or $CH_2NRCOR$;

$R_7$ is independently methyl, ethyl, isopropyl, cyclopropyl, cyclobutyl, or cyclopentyl;

X is $NR_8$;

$R_8$ is independently H, ethyl, n-propyl or n-butyl;

R is independently H, methyl, ethyl, Ph or $CH_2Ph$, wherein the $(R)_2$ in $N(R)_2$ may be a heterocycle containing the nitrogen;

$R_{10}$ is independently H, F, or $CH_3$;

$Ar_1$ is phenyl;

$Ar_2$ is 4-hydroxyphenyl or phenyl; and f is an integer of 2.

14. A compound according to claim 1 wherein:

$R_1$ is independently H or straight or branched alkyl of 1–4 carbons or a carbocycle of 3–5 carbon atoms;

$R_2$ is independently H or straight or branched alkyl of 1–4 carbons or a carbocycle of 3–5 carbon atoms;

$R_3$ is independently $NH_2$, $CH_2OH$, $OCH_2CH_2OH$, or $CH_2CH_2OH$;

$R_4$, $R_5$, and $R_6$ are independently H, $NH_2$, $CH_2OH$, =O when Ar is Het, methyl, ethyl, or isopropyl;

$R_7$ is isopropyl;

X is $NR_8$;

$R_8$ is independently H, ethyl, n-propyl or n-butyl;

$R_{10}$ is independently H, F, or $CH_3$;

$Ar_1$ is phenyl;

$Ar_2$ is phenyl or 4-hydroxyphenyl; and f is an integer of 2.

15. A compound according to claim 1 wherein:

$R_1$ is independently H or straight or branched alkyl of 1–4 carbons or a carbocycle of 3–5 carbon atoms;

$R_2$ is independently H or straight or branched alkyl of 1–4 carbons or a carbocycle of 3–5 carbon atoms, $R_3$ is independently H, $CH_2OH$, $NH_2$, or =O;

$R_4$, $R_5$, and $R_6$ are independently H, OH, $CH_2OH$, $NH_2$, or F;

$R_7$ is independently isopropyl, sec-butyl, isobutyl, or cyclopentyl;

X is $NR_8$;

$R_8$ is independently H, ethyl, n-propyl or n-butyl;

R is independently H, methyl, ethyl, Ph, $CH_2Ph$, and wherein the $(R)_2$ in $N(R)_2$ may be a heterocycle having a nitrogen;

$R_{10}$ is H, F, or $CH_3$;

f is an integer of 2;

$Ar_1$ is phenyl and $Ar_2$ is phenyl or 4-hydroxyphenyl.

16. A pharmaceutical composition for the treatment of infection or disease caused by HIV, which comprises an amount of the compound of claim 1 sufficient to provide an antivirally effective dosage of the compound of Formula I and a pharmaceutically effective carrier.

17. A pharmaceutical composition for the treatment of infection or disease caused by HIV, which comprises an amount of the compound of claim 1 in the range of about 1 to about 50 mg/kg-day or up to 3 g per day and a pharmaceutically effective carrier.

18. A method of treatment of infection or disease caused by HIV, which comprises administering to a subject in need of such treatment a composition of claim 1.

19. A compound according to claim 1 and selected from:

5-Trifluoromethyl-pyridine-2-sulfonic acid {3-[(4-hydroxy-6-isopropyl-2-oxo-6-phenethyl-5,6-dihydro-2H-pyran-3-yl)-propyl-amino]-phenyl}-amide;

5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

5-Trifluoromethyl-pyridine-2-sulfonic acid {3-[ethyl-(4-hydroxy-6-isopropyl-2-oxo-6-phenethyl-5,6-dihydro-2H-pyran-3-yl)-amino]-phenyl}-amide;

5-Trifluoromethyl-pyridine-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

5-Trifluoromethyl-pyridine-2-sulfonic acid [3-(ethyl-{4-hydroxy-6-[2-(4-hydroxy-phenyl)-ethyl]-2-oxo-6-propyl-5,6-dihydro-2H-pyran-3-yl}-amino)-phenyl]-amide;

5-Trifluoromethyl-pyridine-2-sulfonic acid [3-(ethyl-{4-hydroxy-6-[2-(4-hydroxy-phenyl)-ethyl]-6-isopropyl-2-oxo-5,6-dihydro-2H-pyran-3-yl}-amino)phenyl]-amide;

4-Hydroxy-6-[2-(4-hydroxy-phenyl)-ethyl]-6-isopropyl-3-(phenyl-propyl-amino)-5,6-dihydro-pyran-2-one;

6-Cyclopentyl-4-hydroxy-6-[2-(3-hydroxy-phenyl)-ethyl]-3-phenyl-propyl-amino)-5,6-dihydro-pyran-2-one;

4-Hydroxy-6-[2-(2-hydroxymethyl-phenyl)-ethyl]-6-isopropyl-3-(phenyl-propyl-amino)-5,6-dihydro-pyran-2-one;

Thiophene-2-sulfonic acid [3-({4-hydroxy-6-[2-(4-hydroxy-phenyl)-ethyl]-6-isopropyl-2-oxo-5,6-dihydro-2H-pyran-3-yl}-propyl-amino)-phenyl]-amide;

5-Trifluoromethyl-pyridine-2-sulfonic acid [3-({4-hydroxy-6-[2-(phenyethyl)-6-(n-propyl)-2-oxo-5,6-dihydro-2H-pyran-3-yl}-propyl-amino)-phenyl]-amide;

5-Trifluoromethyl-pyridine-2-sulfonic acid [3-({6-cyclopentyl-4-hydroxy-6-[2-(4-hydroxy-phenyl)-ethyl]-2-oxo-5,6-dihydro-2H-pyran-3-yl }-propyl-amino)-phenyl] amide;

3-(Butyl-phenyl-amino)-4-hydroxy-6-[2-(4-hydroxy-phenyl)-ethyl]-6-isopropyl-5,6-dihydro-pyran-2-one;

Pyridine-2-sulfonic acid [3-({4-hydroxy-6-[2-(4-hydroxy-phenyl)-ethyl]-6-isopropyl-2-oxo-5,6-dihydro-2H-pyran-3-yl }-propyl-amino)-phenyl]-amide;

3-(Butyl-phenyl-amino)-4-hydroxy-6-[2-(4-hydroxy-phenyl)-ethyl]-6-isopropyl-5,6-dihydro-pyran-2-one;

3-(Butyl-phenyl-amino)-6-cyclopentyl-4-hydroxy-6-[2-(3-hydroxy-phenyl)-ethyl]-5,6-dihydro-pyran-2-one;

5-Trifluoromethyl-pyridine-2-sulfonic acid [3-({6-[2-(4-amino-phenyl)-ethyl]-4-hydroxy-6-isopropyl-2-oxo-5,6-dihydro-2H-pyran-3-yl}-propyl-amino)-phenyl]-amide;

3-[(3,4-Dichloro-phenyl)-propyl-amino]-4-hydroxy-6-[2-(4-hydroxy-phenyl)-ethyl]-6-isopropyl-5,6-dihydro-pyran-2-one;

4-Hydroxy-3-[(3-hydroxymethyl-phenyl)-propyl-amino]-6-[2-(4-hydroxy-phenyl)-ethyl]-6-isopropyl-5,6-dihydro-pyran-2-one;

6-[2-(4-Amino-phenyl)-ethyl]-3-diphenyamino-4-hydroxy-6-isopropyl-5,6-dihydro-pyran-2-one;

3-({4-Hydroxy-6-[2-(4-hydroxy-phenyl)-ethyl]-6-isopropyl-2-oxo-5,6-dihydro-2H-pyran-3-yl)-phenyl-amino)-propionitrile;

3-Diphenylamino-4-hydroxy-6-[2-(4-hydroxy-phenyl)-ethyl]-6-isopropyl-5,6-dihydro-pyran-2-one;

Pyridine-2-sulfonic acid {3-[ethyl-(4-hydroxy-6-isopropyl-2-oxo-6-phenethyl-5,6-dihydro-2H-pyran-3-yl)-amino]-phenyl}-amide;

4-Hydroxy-6-isopropyl-6-phenethyl-3-(phenyl-propyl-amino)-5,6-dihydro-pyran-2-one;

3-({4-Hydroxy-6-[2-(4-hydroxy-phenyl)-ethyl]-6-isopropyl-2-oxo-5,6-dihydro-2H-pyran-3-yl}-propyl-amino)-benzoic acid methyl ester;

3-[(3,5-Dichloro-phenyl)-propyl-amino]-4-hydroxy-6-[2-(4-hydroxy-phenyl)-ethyl]-6-isopropyl-5,6-dihydro-pyran-2-one;

6-[2-(4-Amino-phenyl)-ethyl]-4-hydroxy-6-isopropyl-3-(phenyl-propyl-amino)5,6-dihydro-pyran-2-one;

4-Hydroxy-6-[2-(4-hydroxy-phenyl)-ethyl]-6-isopropyl-3-(phenyl-propylamino)-5,6-dihydro-pyran-2-one;

4-Hydroxy-6-isopropyl-3-(phenyl-propyl-amino)-6-(2-thiophen-3-yl-ethyl)-5,6-dihydro-pyran-2-one;

6-Cyclopentyl-4-hydroxy-6-[2-(4-hydroxy-phenyl)-ethyl]-3-(phenyl-propyl-amino)-5,6-dihydro-pyran-2-one;

4-Hydroxy-3-[(3-hydroxymethyl-phenyl)-propyl-amino]-6-[2-(4-hydroxy-phenyl)-ethyl]-6-isopropyl-5,6-dihydro-pyran-2-one;

3-(Ethyl-phenyl-amino)-4-hydroxy-6-[2-(4-hydroxy-phenyl)-ethyl]-6-isopropyl-5,6-dihydro-pyran-2-one;

6-Cyclopentyl-3-diphenylamino-4-hydroxy-6-[2-(3-hydroxy-phenyl)-ethyl]-5,6-dihydro-pyran-2-one;

3-(Cyclohexyl-phenyl-amino)-4-hydroxy-6-[2-(4-hydroxy-phenyl)-ethyl]-6-isopropyl-5,6-dihydro-pyran-2-one;

3-(Cyclopentyl-phenyl-amino)-4-hydroxy-6-[2-(4-hydroxy-phenyl)-ethyl]-6-isopropyl-5,6-dihydro-pyran-2-one;

Thiophene-2-sulfonic acid {3-[(4-hydroxy-6-isopropyl-2-oxo-6-phenethyl-5,6-dihydro-2H-pyran-3-yl)-propyl-amino]-phenyl}-amide;

4-Hydroxy-6-[2-(4-hydroxy-phenyl)-ethyl]-6-isopropyl-3-[(4-methoxy-phenyl)-phenyl-amino]-5,6-dihydro-pyran-2-one;

4-Hydroxy-6-[2-(4-hydroxy-phenyl)-ethyl]-6-methyl-3-(phenyl-propyl-amino)-5,6-dihydro-pyran-2-one;

4-Hydroxy-6-[2-(4-hydroxy-phenyl)-ethyl]-3-[(3-hydroxy-phenyl)-phenyl-amino]-6-isopropyl-5,6-dihydro-pyran-2-one;

6-Butyl-4-hydroxy-6-[2-(4-hydroxy-phenyl)-ethyl]-3-(phenyl-propyl-amino)-5,6-dihydro-pyran-2-one;

6-Cyclopropyl-4-hydroxy-6-[2-(4-hydroxy-phenyl)-ethyl]-3-(phenyl-propyl-amino)-5,6-dihydro-pyran-2-one;

4-Hydroxy-6-[2-(4-hydroxy-phenyl)-ethyl]-6-isopropyl-3-(isopropyl-phenyl-amino)-5,6-dihydro-pyran-2-one;

1-Methyl-1H-imidazole-4-sulfonic acid {3-[ethyl-(4-hydroxy-2-oxo-6-phenethyl-6-propyl-5,6-dihydro-2H-pyran-3-yl)-amino]-phenyl }-amide;

3-(Ethyl-p-tolyl-amino)-4-hydroxy-6-[2-(4-hydroxy-phenyl)-ethyl]-6-isopropyl-5,6-dihydro-pyran-2-one;

4-Cyano-N-[3-({4-hydroxy-6-[2-(4-hydroxy-phenyl)-ethyl]-6-methyl-2-oxo-5,6-dihydro-2H-pyran-3-yl }-propyl-amino)-phenyl]-benzenesulfonamide;

4-Hydroxy-3-[(2-hydroxy-ethyl)-phenyl-amino]-6-[2-(4-hydroxy-phenyl)-ethyl]-6-isopropyl-5,6-dihydro-pyran-2-one;

4-Hydroxy-6-[2-(4-hydroxy-phenyl)-ethyl]-6-methyl-3-(propyl-m-tolyl-amino)-5,6-dihydro-pyran-2-one;

1-Methyl-1H-imidazole-4-sulfonic acid [3-(ethyl-{4-hydroxy-6-[2-(4-hydroxy-phenyl)-ethyl]-2-oxo-6-propyl-5,6-dihydro-2H-pyran-3-yl }-amino)-phenyl]-amide;

4-Hydroxy-6-[2-(4-hydroxy-phenyl)-ethyl]-6-isopropyl-3-[(3-methyl-butyl)-phenyl-amino]-5,6-dihydro-pyran-2-one;

3-(Cyclopropyl-phenyl-amino)-4-hydroxy-6-[2-(4-hydroxy-phenyl)-ethyl]-6-isopropyl-5,6-dihydro-pyran-2-one;

3-(tert-Butyl-phenyl-amino)-4-hydroxy-6-[2-(4-hydroxy-phenyl)-ethyl]-6-isopropyl-5,6-dihydro-pyran-2-one;

(S)-3-[(4-Fluoro-phenyl)-isopropyl-amino]-4-hydroxy-6-[2-(4-hydroxy-phenyl)-ethyl]-6-isopropyl-5,6-dihydro-pyran-2-one;

3-[(3-Amino-phenyl)-ethyl-amino]-4-hydroxy-6-isopropyl-6-phenethyl-5,6-dihydro-pyran-2-one;

3-(Ethyl-o-tolyl-amino)-4-hydroxy-6-[2-(4-hydroxy-phenyl)-ethyl]-6-isopropyl-5,6-dihydro-pyran-2-one;

3-(Benzyl-phenyl-amino)-4-hydroxy-6-[2-(4-hydroxy-phenyl)-ethyl]-6-isopropyl-5,6-dihydro-pyran-2-one;

Dimethyl-sulfamic acid 3-({4-hydroxy-6-[2-(4-hydroxy-phenyl)-ethyl]-6-methyl-2-oxo-5,6-dihydro-2H-pyran-3-yl}-propyl-amino)-phenyl ester;

[3-(3,4-Dihydro-2H-quinoxalin-1-yl)-4-hydroxy-6-[2-(4-hydroxy-phenyl)-ethyl]-6-methyl-5,6-dihydro-pyran-2-one;]

6-Cyclohexyl-4-hydroxy-6-[2-(4-hydroxy-phenyl)-ethyl]-3-(phenyl-propyl-amino)-5,6-dihydro-pyran-2-one;

6-Cyclopentyl-3-diphenylamino-4-hydroxy-[2-(4-hydroxy-phenyl)-ethyl]-5,6-dihydro-pyran-2-one;

[3-[(3,5-Dichloro-phenyl)-propyl-amino]-4-hydroxy-6-[2-(4-hydroxy-phenyl)ethyl]-6-isopropyl-5,6-dihydro-pyran-2-one;]

6-(2-Furan-3-yl-ethyl)-4-hydroxy-6-[4-(2-hydroxy-ethoxy)-phenyl]-3-phenyl-propyl-amino]-5,6-dihydro-pyran-2-one;

6-Cyclopentyl-3-(ethyl-phenyl-amino)-4-hydroxy-6-[2-(4-hydroxy-phenyl)-ethyl]-5,6-dihydro-pyran-2-one;

[2-(4-Amino-phenyl)-ethyl]-(ethyl-phenyl-amino)-hydroxy-isopropyl-5,6-dihydro-pyran-2-one;

3-[Butyl-(3,5-dichloro-phenyl)-amino]-4-hydroxy-6-[2-(4-hydroxy-phenyl)-ethyl]-6-isopropyl-5,6-dihydro-pyran-2-one;

3-[(3-Chloro-phenyl)-propyl-amino]-4-hydroxy-6-[4-(2-hydroxy-ethoxy)-phenyl]-6-phenethyl-5,6-dihydro-pyran-2-one;

Pyridine-2-sulfonic acid {3-[ethyl-(4-hydroxy-2-oxo-6-phenethyl-6-propyl-5,6-dihydro-2H-pyran-3-yl)-amino]-phenyl}-amide;

6-Cyclopropyl-3-(ethyl-phenyl-amino)-4-hydroxy-[2-(4-hydroxy-phenyl)-ethyl]-5,6-dihydro-pyran-2-one;

4-Hydroxy-6-[4-(2-hydroxy-ethoxy)-phenyl]-6-phenethyl-3-(phenyl-propyl-amino)-5,6-dihydro-pyran-2-one;

4-Hydroxy-6-[2-(4-hydroxy-phenyl)-ethyl]-6-phenethyl-3-(phenyl-propyl-amino)-5,6-dihydro-pyran-2-one;

6-(2-Cyclopentyl-ethyl)-4-hydroxy-6-[4-(2-hydroxy-ethoxy)-phenyl]-3-(phenyl-propyl-amino)-5,6-dihydro-pyran-2-one;

6-Ethyl-4-hydroxy-6-[2-(4-hydroxy-phenyl)-ethyl]-3-(phenyl-propyl-amino)-5,6-dihydro-pyran-2-one;

4-Hydroxy-6-[2-(4-hydroxy-phenyl)-ethyl]-3-(phenyl-propyl-amino)-6-[4-(2-piperazin 1-yl-ethoxy)-phenyl]-5,6-dihydropyran-2-one;

3-Diphenylamino-4-hydroxy-6-[2-(4-hydroxy-phenyl)-ethyl]-6-isopropyl-5,6-dihydro-pyran-2-one;

4-Hydroxy-6-[4-(2-hydroxy-ethoxy)-phenyl]-6-phenyl-3-(phenyl-propyl-amino)-5,6-dihydro-pyran-2-one;

4-Hydroxy-6-[2-(4-hydroxy-phenyl)-ethyl]-3-(phenyl-propyl-amino)-6-propyl-5,6-dihydro-pyran-2-one;

6-[2-(4-Amino-phenyl)-ethyl]-4-hydroxy-6-phenyl-3-(phenyl-propyl-amino)-5,6-dihydro-pyran-2-one;

4-Hydroxy-6-(4-methoxymethoxy-phenyl)-6-phenyl-3-(phenyl-propyl-amino)-5,6-dihydro-pyran-2-one;

Thiophene-2-sulfonic acid {3-[ethyl-(4-hydroxy-6-isopropyl-2-oxo-6-phenethyl-5,6-dihydro-2H-pyran-3-yl)-amino]-phenyl}-amide;

6-Cyclopropyl-3-(ethyl-phenyl-amino)-4-hydroxy-6-[2-(4-hydroxy-phenyl)-ethyl]-5,6-dihydro-pyran-2-one;

6-Cyclopentyl-3-(ethyl-phenyl-amino)-4-hydroxy-6-[2-(4-hydroxy-phenyl)-ethyl]-5,6-dihydro-pyran-2-one;

3-Diphenlylamino-4-hydroxy-6-[2-(4-hydroxy-phenyl)-ethyl]-6-propyl-5,6-dihydro-pyran-2-one;

4-Hydroxy-3-[(3-methylsulfanyl-phenyl)-propyl-amino]-6-phenethyl-6-phenyl-5,6-dihydro-pyran-2-one;

Dimethyl-sulfamic acid 3-({4-hydroxy-6-[4-(2-hydroxy-ethoxy)-phenyl]-2-oxo-6phenethyl-5,6-dihydro-2H-pyran-3-yl}-propyl-amino)-phenyl ester;

3-(Butyl-phenyl-amino)-4-hydroxy-6-phenethyl-6-phenyl-5,6-dihydro-pyran-2-one;

3-Diphenylamino-4-hydroxy-6-phenethyl-6-phenyl-5,6-dihydro-pyran-2-one;

1-Methyl-1H-imidazole-4-sulfonic acid [3-({4-hydroxy-6-[2-(4-hydroxy-phenyl)-ethyl]-6-methyl-2-oxo-5,6-dihydro-2H-pyran-3-yl }-propyl-amino)-phenyl]-amide;

4-Hydroxy-6-phenethyl-6-phenyl-3-(propyl-m-tolyl-amino)-5,6-dihydro-pyran-2-one;

4-Hydroxy-6-phenethyl-6-phenyl-3-(phenyl-propyl-amino)-5,6-dihydro-pyran-2-one;

4-Hydroxy-3-[(3-hydroxymethyl-phenyl)-propyl-amino]-6-[2-(4-hydroxy-phenyl)-ethyl]-6-methyl-5,6-dihydro-pyran-2-one;

4-Hydroxy-6-pentyl-6-phenyl-3-(phenyl-propyl-amino)-5,6-dihydro-pyran-2-one;

4-Hydroxy-6-[4-(2-hydroxy-ethoxy)-phenyl]-3-[(3-hydroxy-phenyl)-propyl-amino]-6-phenethyl-5,6-dihydro-pyran-2-one;

3-[(4-Hydroxy-2-oxo-6-phenethyl-6-phenyl-5,6-dihydro-2H-pyran-3-yl)-propyl-amino]-benzoic acid methyl ester;

N-(3-{2-[4-Hydroxy-6-oxo-2-phenyl-5-(phenyl-propyl-amino)-3,6-dihydro-2H-pyran-2-yl]-ethyl}-phenyl)-acetamide;

4-Hydroxy-3-[(3-hydroxymethyl-phenyl)-propyl-amino]-6-phenethyl-6-phenyl-5,6-dihydro-pyran-2-one;

4-Hydroxy-6-[4-(2-hydroxy-ethoxy)-phenyl]-3-(phenyl-propyl-amino)-6-[2-(tetrahydro-furan-3-yl)-ethyl]-5,6-dihydro-pyran-2-one;

5-({4-Hydroxy-6-[2-(4-hydroxy-phenyl)-ethyl]-6-isopropyl-2-oxo-5,6-dihydro-2H-pyran-3-yl}-propyl-amino)-isophthalic acid dimethyl ester;

4-Hydroxy-6-[2-(2-hydroxymethyl-phenyl)-ethyl]-3-[(3-hydroxymethyl-phenyl)-phenyl-amino]-6-isopropyl-5,6-dihydro-pyran-2-one;

3-Diphenylamino-4-hydroxy-6-[2-(4-hydroxy-phenyl)-ethyl]-6-methyl-5,6-dihydro-pyran-2-one;

N-(4-{2-[4-Hydroxy-6-oxo-2-phenyl-5-(phenyl-propyl-amino)-3,6-dihydro-2H-pyran-2-yl]-ethyl}-phenyl)-acetamide;

4-Hydroxy-3-{[3-(2-hydroxy-ethoxy)-phenyl]-propyl-amino}-6-phenethyl-6-phenyl-5,6-dihydro-pyran-2-one;

3-(Ethyl-phenyl-amino)-4-hydroxy-6-[2-(4-hydroxy-phenyl)-ethyl]-6-methyl-5,6-dihydro-pyran-2-one;

3-(Ethyl-phenyl-amino)-4-hydroxy-6-[2-(4-hydroxy-phenyl)-ethyl]-6-propyl-5,6-dihydro-pyran-2-one;

(R)-4-Hydroxy-6-isopropyl-6-phenethyl-3-(phenyl-propyl-amino)-5,6-dihydro-pyran-2-one;

4-Hydroxy-6-phenethyl-6-phenyl-3-o-tolylamino-5,6-dihydro-pyran-2-one;

4-Hydroxy-3-(2-isopropyl-phenylamino)-6-phenethyl-6-phenyl-5,6-dihydro-pyran-2-one;

4-Hydroxy-3-(2-isopropyl-phenylamino)-6,6-diphenyl-5,6-dihydro-pyran-2-one;

3-(2-tert-Butyl-5-methyl-phenylamino)-4-hydroxy-6-phenethyl-6-phenyl-5,6-dihydro-pyran-2-one;

3-(2-tent-Butyl-5-methyl-phenylamino)-4-hydroxy-6,6-diphenyl-5,6-dihydro-pyran-2-one;

3-(Ethyl-phenyl-amino)-4-hydroxy-6-phenethyl-6-phenyl-5,6-dihydro-pyran-2-one;

4-Hydroxy-3-(isopropyl-phenyl-amino)-6-phenethyl-6-phenyl-5,6-dihydro-pyran-2-one;

4-Hydroxy-3-(methyl-phenyl-amino)-6-phenethyl-6-phenyl-5,6-dihydro-pyran-2-one;

4-Hydroxy-3-(isobutyl-phenyl-amino)-6-phenethyl-6-phenyl-5,6-dihydro-pyran-2-one;

4-Hydroxy-6-phenethyl-6-phenyl-3-(phenyl-propyl-amino)-5,6-dihydro-pyran-2-one;

3-(Allyl-phenyl-amino)-4-hydroxy-6-phenethyl-6-phenyl-5,6-dihydro-pyran-2-one;

3-(Benzyl-phenyl-amino)-4-hydroxy-6-phenethyl-6-phenyl-5,6-dihydro-pyran-2-one;

3-(Cyclopropylmethyl-phenyl-amino)-4-hydroxy-6-phenethyl-6-phenyl-5,6-dihydro-pyran-2-one;

4-Hydroxy-6-[4-(2-hydroxy-ethoxy)-phenyl]-6-methyl-3-(phenyl-propyl-amino)-5,6-dihydro-pyran-2-one;

4-Hydroxy-6-[2-(4-hydroxy-phenyl)-1,1-dimethyl-ethyl]-6-methyl-3-(phenyl-propyl-amino)-5,6-dihydro-pyran-2-one;

4-Hydroxy-3-[(2-methoxy-phenyl)-propyl-amino]-6-phenethyl-6-phenyl-5,6-dihydro-pyran-2-one;

3-(2-tert-Butyl-phenylamino)-4-hydroxy-6-phenethyl-6-phenyl-5,6-dihydro-pyran-2-one;

4-Hydroxy-3-[(2-hydroxy-ethyl)-phenyl-amino]-6-phenethyl-6-phenyl-5,6-dihydro-pyran-2-one;

[(4-Hydroxy-2-oxo-6-phenethyl-6-phenyl-5,6-dihydro-2H-pyran-3-yl)-phenyl-amino]-acetic acid ethyl ester;

3-[(3-Ethyl-phenyl)-propyl-amino]-4-hydroxy-6-phenethyl-6-phenyl-5,6-dihydro-pyran-2-one;

4-Hydroxy-3-{[3-(2-hydroxy-ethoxy)-phenyl]-propyl-amino}-6-[2-(4-hydroxy-phenyl)-ethyl]-6-methyl-5,6-dihydro-pyran-2-one;

3-({4-Hydroxy-6-[2-(4-hydroxy-phenyl)-ethyl]-6-methyl-2-oxo-5,6-dihydro-2H-pyran 3-yl}-propyl-amino)-benzoic acid methyl ester;

[3-({4-Hydroxy-6-[2-(4-hydroxy-phenyl)-ethyl]-6-methyl-2-oxo-5,6-dihydro-2H-pyran-3-yl}-propyl-amino)-phenyl]-carbamic acid tert-butyl ester;

4-Hydroxy-6-[2-(4-hydroxy-phenyl)-ethyl]-3-[(3-hydroxy-phenyl)-propyl-amino]-6-methyl-5,6-dihydro-pyran-2-one;

4-Hydroxy-6-[2-(4-hydroxy-phenyl)-ethyl]-6-methyl-3-(methyl-phenyl-amino)-5,6-dihydro-pyran-2-one;

3-[(3-Amino-phenyl)-ethyl-amino]-4-hydroxy-6-phenethyl-6-propyl-5,6-dihydro-pyran-2-one;

3-[(3-Amino-phenyl)-ethyl-amino]-4-hydroxy-6-[2-(4-hydroxy-phenyl)-ethyl]-6-isopropyl-5,6-dihydro-pyran-2-one;

3-Diphenylamino-4-hydroxy-6-isopropyl-6-phenethyl-5,6-dihydro-pyran-2-one;

3-(Ethyl-phenyl-amino)-4-hydroxy-6-isopropyl-6-phenethyl-5,6-dihydro-pyran-2-one;

6-(3-Amino-propyl-phenyl)-4-hydroxy-6-methyl-3-(phenyl-propyl-amino)-5,6-dihydro-pyran-2-one; and 6-Cyclopentyl-4-hydroxy-3-[(3-hydroxymethyl-phenyl)-propyl-amino]-6-[2-(3-hydroxy-phenyl)-ethyl]-5,6-dihydro-pyran-2-one.

20. A compound according to claim 1 and selected from:

4-Hydroxy-3-(2-isopropylphenylamino)-6-phenethyl-6-phenyl-5,6-dihydro-pyran-2-one;

3-(2-tert-Butyl-5-methyl)-phenylamino)-4-hydroxy-6-phenethyl-6-phenyl-5,6-dihydro-pyran-2-one; and 3-(2-tert-Butyl-4-hydroxymethyl-5-methyl)-phenylamino)-4-hydroxy-6-phenethyl-6-phenyl-5,6-dihydro-pyran-2-one.

* * * * *

UNITED STATES PATENT AND TRADEMARK OFFICE
CERTIFICATE OF CORRECTION

PATENT NO.     : 6,512,006 B1
DATED          : January 28, 2003
INVENTOR(S)    : Frederick Earl Boyer, Jr. et al.

It is certified that error appears in the above-identified patent and that said Letters Patent is hereby corrected as shown below:

Column 38,
Line 63, "$[C(R_9\ 2]_nR, [C(R_9)_2]_n(O)COR, O[C(R_9)_2]_mOR, N(R)$" should read -- $[C(R_92]_nR, [C(R_9)_2]_n(O)COR, O[C(R_9)_2]_mOR, N(R)$ --

Column 39,
Line 1, "$[C(R_9)\ _2]_nOSO_2N(R)_2, [C(R_9)_2]_nN(R_9)SO_2N(R)_2,$" should read -- $[C(R_9)_2]_nOSO_2N(R)_2, [C(R_9)_2]_nN(R_9)SO_2N(R)_2,$ --
Line 66, "$[C(R_9)_2)_nOSO_2N(R)_2\ [C(R_9)_2]_nN(R_9)SO_2OR,$" should read -- $[C(R_9)_2)_nSO_2N(R)_2\ [C(R_9)_2]_nN(R_9)SO_2OR,$ --

Column 40,
Line 45, "$(CH_2)_nOR, (CH_2)_nN(R)_2, F, Cl, Cr, ==O, (CF_2)_nN(R_9)$" should read -- $(CH_2)_nOR, (CH_2)_nN(R)_2, F, Cl, Cr, ==O, (CH_2)_nN(R_9)$ --
Line 48, "$(CH_2)_nN(R)SO_2R, (CH_2)_nN(R_9)SO_2, OR,$" should read -- $(CH_2)_nN(R_9)SO_2R, (CH_2)_nN(R_9)SO_2, OR$ --

Column 41,
Line 27, "$AR_2$ is 4hydroxyphenyl or phenyl; and" should read -- $AR_2$ is 4-hydroxyphenyl or phenyl; and --

Column 50,
Line 12, "methyl-2-oxo-5,6-dihydro-2H-pyran 3-yl}-propyl-" should read -- methyl-2-oxo-5,6-dihydro-2H-pyran-3-yl}-propyl- --

Signed and Sealed this

Twelfth Day of August, 2003

JAMES E. ROGAN
*Director of the United States Patent and Trademark Office*